(12) United States Patent
Heiser et al.

(10) Patent No.: US 9,610,368 B2
(45) Date of Patent: Apr. 4, 2017

(54) RADIOLABELLED GLUTAMINYL CYCLASE (QC) INHIBITORS AND USES OF SAME

(71) Applicant: Probiodrug AG, Halle/Saale (DE)

(72) Inventors: Ulrich Heiser, Halle/Saale (DE); Daniel Ramsbeck, Halle/Saale (DE); Hans-Ulrich Demuth, Halle/Saale (DE)

(73) Assignee: PROBIODRUG AG, Halle Saale (DE)

( * ) Notice: Subject to any disclaimer, the term of this patent is extended or adjusted under 35 U.S.C. 154(b) by 332 days.

(21) Appl. No.: 14/570,350

(22) Filed: Dec. 15, 2014

(65) Prior Publication Data

US 2015/0104389 A1 Apr. 16, 2015

Related U.S. Application Data

(63) Continuation of application No. 13/479,826, filed on May 24, 2012, now Pat. No. 8,945,510.

(60) Provisional application No. 61/490,654, filed on May 27, 2011.

(51) Int. Cl.
*A61K 51/04* (2006.01)
*C07B 59/00* (2006.01)

(52) U.S. Cl.
CPC ........ *A61K 51/0453* (2013.01); *C07B 59/002* (2013.01)

(58) Field of Classification Search
CPC ............................... A61K 31/41; A61K 51/12
See application file for complete search history.

(56) References Cited

U.S. PATENT DOCUMENTS

| | | | | |
|---|---|---|---|---|
| 5,304,367 A | * | 4/1994 | Biegon | A61K 51/1282 424/1.11 |
| 7,304,086 B2 | * | 12/2007 | Schilling | A61K 31/4164 514/367 |
| 2010/0028918 A1 | | 2/2010 | Demuth et al. | |
| 2011/0092501 A1 | | 4/2011 | Heiser et al. | |

FOREIGN PATENT DOCUMENTS

| | | |
|---|---|---|
| WO | WO 2007/124345 | 11/2007 |
| WO | WO 2010/012828 | 2/2010 |
| WO | WO 2010/026212 | 3/2010 |
| WO | WO 2011/029920 | 3/2011 |

OTHER PUBLICATIONS

IUPAC report ofr Isotopic Masses and Natural Abundances, 1997.*
Bockers et al., Glutaminyl-Cyclase Expression in the Bovine/Porcine Hypothalamus and Pituitary, J Neuroendocrinol, 1995, pp. 445-453, vol. 7.
Buchholz et al., Inhibitors for Human Glutaminyl Cyclase by Structure Based Design and Bioisosteric Replacement, J Med Chem, 2009, pp. 7069-7080, vol. 52.
Busby et al., An Enzyme(s) That Converts Glutaminyl-peptides into Pyroglutamyl-peptides, in the Journal of Biological Chemistry, 1987, pp. 8532-8536, vol. 262, No. 18.
Cai et al., Synthesis and Evaluation of Two 18F-Labeled 6-lodo-2-(4'-N,Ndimethylamino) phenylimidizol[1,2-α]pyridine Derivatives as Prospective Radioligands for β-Amyloid in Alzheimer's Disease, J Med Chem, 2004, pp. 2208-2218, vol. 47.
Consalvo et al., A Rapid Fluorometric Assay for N-Terminal Glutaminyl Cyclase Activity Using High-Performance Liquid Chromatography, Analytical Biochemistry, 1988, pp. 131-138, vol. 175.
Dahl et al., Carica papaya Glutamine Cyclotransferase Belongs to a Novel Plant Enzyme Subfamily: Cloning and Characterization of the Recombinant Enzyme, Protein Expression and Purification, 2000, pp. 27-36, vol. 20.
El Moussaoui et al., Revisiting the enzymes stored in the laticifers of Carica papaya in the context of their possible participation in the plant defence mechanism, CMLS Cellular and Molecular Life Sciences, 2001, pp. 556-570, vol. 56.
FDA Panel Backs Amyvid (Florbetapir) Approval, 2011, downloaded from www.medchemist.com/2011/01/fda-panel-backs-amyvid-florbetapir.html on Aug. 26, 2011, 1 page.
Fischer et al., Identification of a mammalian glutaminyl cyclase converting glutaminyl into pyroglutamyl peptides, Pro. Natl. Acad. Sci. USA, 1987, pp. 3628-3632, vol. 84.
Gololobov et al., Substrate and inhibitor specificity of glutamine cyclotransferase (QC), Biol Chem Hoppe Seyler, 1996, pp. 395-398, vol. 377, No. 6.
Messer, Enzymatic Cyclization of L-Glutamine and L-Glutaminyl Peptides, Nature, 1963, p. 1299, vol. 197, No. 4874.
Nelissen et al., Phase 1 Study of the Pittsburgh Compound B Derivative 18FFlutemetamol in Healthy Volunteers and Patients with Probable Alzheimer Disease, J Nucl Med, 2009, vol. 50, No. 8.
Pohl et al, Primary structure and functional expression of a glutaminyl cyclase, Proc in Natl Acad Sci USA, 1991, pp. 10059-10063, vol. 88.
Winstead et al., Relationship of Molecular Structure to in Vivo Scintigraphic Distribution Patterns of Carbon-11 Labeled Compounds. 3. [11C]Hydantoins, J Med Chem, 1976, vol. 19, No. 2.

* cited by examiner

*Primary Examiner* — Michael G Hartley
*Assistant Examiner* — Jagadishwar Samala
(74) *Attorney, Agent, or Firm* — Dentons US LLP

(57) ABSTRACT

Radiolabeled glutaminylcyclase (QC) inhibitors as imaging agents, in particular, but not exclusively, as medical imaging agents for the detection of neurological disorders; and pharmaceutical compositions, methods and kits for detecting neurological disorders, using the radiolabeled inhibitors.

17 Claims, 2 Drawing Sheets

RADIOLABELLED GLUTAMINYL CYCLASE (QC) INHIBITORS AND USES OF SAME

CROSS-REFERENCE TO RELATED APPLICATIONS

This application is a Continuation of U.S. application Ser. No. 13/479,826 filed on May 24, 2012, which in turn claims priority to U.S. Provisional Application Ser. No. 61/490,654, filed on May 27, 2011, each of which is incorporated herein by reference in its entirety to the extent permitted by law.

FIELD OF THE INVENTION

The present disclosure relates to the use of radiolabeled glutaminyl cyclase (QC) inhibitors as imaging agents, in particular but not exclusively as medical imaging agents for the detection of neurological disorders. The present disclosure also relates to pharmaceutical compositions comprising said radiolabeled inhibitors and to methods and kits for detecting neurological disorders.

BACKGROUND OF THE INVENTION

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant *Carica papaya* in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer, W. H. and Spiess, J. 1987 Proc Natl Acad Sci USA 84, 3628-3632). For the mammalian QC, the conversion of Gln into pGlu by QC could be shown for the precursors of TRH and GnRH (Busby, W. H. J. et al. 1987 J Biol Chem 262, 8532-8536; Fischer, W. H. and Spiess, J. 1987 Proc Natl Acad Sci USA 84, 3628-3632). In addition, initial localization experiments of QC revealed a co-localization with its putative products of catalysis in bovine pituitary, further improving the suggested function in peptide hormone synthesis (Bockers, T. M. et al. 1995 J Neuroendocrinol 7, 445-453). In contrast, the physiological function of the plant QC is less clear. In the case of the enzyme from *C. papaya*, a role in the plant defense against pathogenic microorganisms was suggested (El Moussaoui, A. et al. 2001 Cell Mol Life Sci 58, 556-570). Putative QCs from other plants were identified by sequence comparisons recently (Dahl, S. W. et al. 2000 Protein Expr Purif 20, 27-36). The physiological function of these enzymes, however, is still ambiguous.

The QCs known from plants and animals show a strict specificity for L-Glutamine in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from *C. papaya* and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed $Glu_1$-conversion is favored around pH 6.0 while $Gln_1$-conversion to pGlu-derivatives occurs with a pH-optimum of around 8.0. Since the formation of pGlu-Aβ-related peptides can be suppressed by inhibition of recombinant human QC and QC-activity from pig pituitary extracts, the enzyme QC is a target in drug development for treatment of Alzheimer's disease.

Alzheimer's disease (AD) is the most common form of dementia and is an incurable, degenerative, and terminal disease. In 2006, there were 26.6 million sufferers worldwide. Alzheimer's is predicted to affect 1 in 85 people globally by 2050. Alzheimer's disease is usually diagnosed clinically from the patient history, collateral history from relatives, and clinical observations, based on the presence of characteristic neurological and neuropsychological features and the absence of alternative conditions. Assessment of intellectual functioning including memory testing can further characterise the state of the disease.

More recently, imaging has become a valuable tool in the diagnosis of Alzheimer's disease. For example, when available as a diagnostic tool, single photon emission computed tomography (SPECT) and positron emission tomography (PET) neuroimaging may be used to confirm a diagnosis of Alzheimer's in conjunction with evaluations involving mental status examination. In a person already having dementia, SPECT appears to be superior in differentiating Alzheimer's disease from other possible causes, compared with the usual attempts employing mental testing and medical history analysis.

A new technique known as PiB PET has been developed for directly and clearly imaging β-amyloid deposits in vivo using a tracer that binds selectively to the Aβ deposits. The PiB-PET compound uses $^{11}C$ PET scanning. Recent studies suggest that PiB-PET is 86% accurate in predicting which people with mild cognitive impairment will develop Alzheimer's disease within two years, and 92% accurate in ruling out the likelihood of developing Alzheimer's.

A similar PET scanning radiopharmaceutical compound called (E)-4-(2-(6-(2-(2-(2-([$^{18}$F]-fluoroethoxy)ethoxy)ethoxy)pyridin-3-yl)vinyl)-N-methyl benzenamine (also known as $^{18}$F AV-45, florbetapir-fluorine-18 or florbetapir), contains the longer-lasting radionuclide fluorine-18, has recently been created, and tested as a possible diagnostic tool in Alzheimer's patients. Florbetapir, like PiB, binds to β-amyloid, but due to its use of fluorine-18 has a half-life of 110 minutes, in contrast to PiB's radioactive half life of 20 minutes. It has also been found that the longer life allowed the tracer to accumulate significantly more in the brains of the AD patients, particularly in the regions known to be associated with beta-amyloid deposits.

There is therefore a need for further imaging agents which are capable of diagnosing neurological disorders such as Alzheimer's disease.

SUMMARY OF THE INVENTION

Among the various aspects of the present disclosure is the provision of a radiolabeled glutaminylcyclase (QC) inhibitor for use as an imaging agent.

The present teachings include radiolabeled glutaminylcyclase (QC) inhibitor compounds of formula (I):

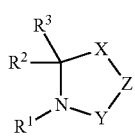
(I)

or a pharmaceutically acceptable salt, solvate or polymorph thereof, including all tautomers and stereoisomers thereof wherein: $R^1$ represents heteroaryl, -carbocyclyl-heteroaryl, —$C_{2-6}$alkenylheteroaryl, —$C_{1-6}$alkylheteroaryl, or $(CH_2)_aCR^5R^6(CH_2)_b$heteroaryl wherein a and b independently represent integers 0-5 provided that a+b=0-5 and $R^5$ and $R^6$ are alkylene which together with the carbon to which they are attached form a $C_3$-$C_5$cycloalkyl group; in which any of aforesaid heteroaryl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —$C(O)OH$, —$NH_2$, —$NHC_{1-4}$alkyl, —$N(C_{1-4}$alkyl$)(C_{1-4}$alkyl$)$, —$C(O)N(C_{1-4}$alkyl$)(C_{1-4}$alkyl$)$, —$C(O)NH_2$, —$C(O)NH(C_{1-4}$alkyl$)$ and —$C(O)NH(C_{3-10}$cycloalkyl$)$; and in which any of aforesaid carbocyclyl groups may optionally be substituted by one or more groups selected from $C_{1-4}$alkyl, oxo, halogen and $C_{1-4}$alkoxy; $R^2$ represents H, $C_{1-8}$alkyl, aryl, heteroaryl, carbocyclyl, heterocyclyl, —$C_{1-4}$alkylaryl, —$C_{1-4}$alkylheteroaryl, —$C_{1-4}$alkylcarbocyclyl or —$C_{1-4}$alkylheterocyclyl; in which any of aforesaid aryl and heteroaryl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, $C_{1-6}$alkoxy-$C_{1-6}$alkoxy-, nitro, halogen, halo$C_{1-6}$alkyl, halo$C_{1-6}$alkoxy, cyano, hydroxyl, —$C(O)OH$, —$NH_2$, —$NHC_{1-4}$alkyl, —$N(C_{1-4}$alkyl$)(C_{1-4}$alkyl$)$, —$N(C_{1-4}$alkyl$)(C_{1-4}$alkyl$)$-N$(C_{1-4}$alkyl$)(C_{1-4}$alkyl$)$, —$C_{1-4}$alkyl-$N(C_{1-4}$alkyl$)(C_{1-4}$alkyl$)$, —$C_{1-4}$alkoxy-$N(C_{1-4}$alkyl$)(C_{1-4}$alkyl$)$, —$N(C_{3-8}$cycloalkyl$)(C_{3-8}$cycloalkyl$)$, —$N(—C_{1-6}$alkyl-$C_{1-6}$alkoxy$)(—C_{1-6}$alkyl-$C_{1-6}$alkoxy$)$, —$C(O)N(C_{1-4}$alkyl$)(C_{1-4}$alkyl$)$, —$C(O)NH_2$, —$C(O)NH(C_{1-4}$alkyl$)$ and —$C(O)NH(C_{3-10}$cycloalkyl$)$; and in which any of aforesaid carbocyclyl and heterocyclyl groups may optionally be substituted by one or more groups selected from $C_{1-4}$alkyl, oxo, halogen, —$C(O)C_{1-6}$alkyl and $C_{1-4}$alkoxy; or $R^2$ represents phenyl substituted by phenyl, phenyl substituted by a monocyclic heteroaryl group, phenyl substituted by phenoxy, phenyl substituted by heterocyclyl, phenyl substituted by heterocyclyl wherein said heterocyclyl is substituted by phenyl, phenyl substituted by —O—$C_{1-4}$alkyl-heterocyclyl, phenyl substituted by benzyloxy, phenyl substituted by carbocyclyl, phenyl substituted by carbocyclyl wherein said carbocyclyl is substituted by heterocyclyl, phenyl substituted by —O-carbocyclyl, heterocyclyl substituted by phenyl, carbocyclyl substituted by phenyl, phenyl fused to carbocyclyl, phenyl fused to heterocyclyl, —$C_{1-4}$alkyl(phenyl substituted by phenyl), —$C_{1-4}$alkyl(phenyl substituted by a monocyclic heteroaryl group), —$C_{1-4}$alkyl(phenyl substituted by a monocyclic heterocyclyl group), —$C_{1-4}$alkyl(phenyl substituted by an —O-carbocyclyl group), —$C_{1-4}$alkyl(phenyl substituted by benzyloxy), —$C_{1-4}$alkyl(optionally substituted phenyl fused to optionally substituted carbocyclyl or —$C_{1-4}$alkyl(optionally substituted phenyl fused to optionally substituted heterocyclyl); in which any of aforesaid phenyl, benzyloxy and heteroaryl groups may optionally be substituted by one or more groups selected from $C_{1-4}$alkyl, halogen and $C_{1-4}$alkoxy, and in which any of aforesaid carbocyclyl and heterocyclyl groups may optionally be substituted by one or more groups selected from methyl, phenyl, oxo, halogen, hydroxyl and $C_{1-4}$alkoxy; $R^3$ represents H, —$C_{1-4}$alkyl or aryl; in which aforesaid aryl may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —$C(O)OH$, —$NH_2$, —$NHC_{1-4}$alkyl, —$N(C_{1-4}$alkyl$)(C_{1-4}$alkyl$)$, —$C(O)N(C_{1-4}$alkyl$)(C_{1-4}$alkyl$)$, —$C(O)NH_2$, —$C(O)NH(C_{1-4}$alkyl$)$ and, —$C(O)NH(C_{3-10}$cycloalkyl$)$; or $R^2$ and $R^3$ are joined to form a carbocyclyl ring which is optionally substituted by one or more $C_{1-2}$alkyl groups; or $R^2$ and $R^3$ are joined to form a carbocyclyl ring which is fused to phenyl, wherein aforesaid carbocyclyl and/or phenyl may optionally be substituted by one or more groups selected from $C_{1-4}$alkyl, halogen and $C_{1-4}$alkoxy; or $R^2$ and $R^3$ are joined to form a carbocyclyl ring which is fused to monocyclic heteroaryl, wherein aforesaid carbocyclyl and/or heteroaryl may optionally be substituted from one or more groups selected from $C_{1-4}$alkyl, halogen and $C_{1-4}$alkoxy; X represents C=O, O, S, $CR^7R^8$, —O—$CH_2$— or —$CH_2$—$CH_2$—; Y represents $CHR^9$, C=O or C=S; Z represents —N—$R^4$, O or $CHR^{10}$, such that when X represents O or S, Z must represent $CHR^{10}$; or X and Z represent two adjacent carbon atoms of a phenyl ring which is fused in that position and which is optionally substituted by one or more halogen or $C_{1-2}$alkyl groups; $R^4$ represents H, —$C_{1-8}$alkyl, —$C(O)C_{1-6}$alkyl or —$NH_2$; $R^7$ and $R^8$ independently represent H, —$C_{1-4}$ alkyl or aryl; in which said aforesaid aryl may be optionally substituted by $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —$C(O)OH$, —$NH_2$, —$NHC_{1-4}$alkyl, —$N(C_{1-4}$alkyl$)(C_{1-4}$alkyl$)$, —$C(O)N(C_{1-4}$alkyl$)(C_{1-4}$alkyl$)$, —$C(O)NH_2$, —$C(O)NH(C_{1-4}$alkyl$)$ and, —$C(O)NH(C_{3-10}$cycloalkyl$)$; $R^9$ and $R^{10}$ independently represent H or methyl; provided that the moiety —Y—Z—X— represents a moiety other than —C(=O)—N(—$R^4$)—C(=O)— or —C(=S)—N(—$R^4$)—C(=O)—.

The present teachings include radiolabeled glutaminylcyclase (QC) inhibitor compounds of formula (II):

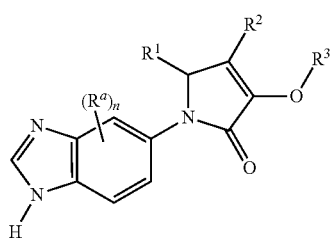
(II)

or a pharmaceutically acceptable salt, solvate or polymorph thereof, including all tautomers and stereoisomers thereof wherein: $R^1$ represents —$C_{1-6}$alkyl, -aryl, —$C_{1-6}$alkylaryl, -cycloalkyl, —$C_{1-6}$alkylcycloalkyl, -heteroaryl, —$C_{1-6}$alkylheteroaryl, -heterocyclyl, —$C_{1-6}$alkylheterocyclyl, -cycloalkyl substituted by phenyl, -cycloalkyl substituted by phenoxy, -phenyl substituted by cycloalkyl, -phenyl substituted by phenoxy, -phenyl substituted by phenyl, heterocyclyl substituted by phenyl, heteroaryl substituted by phenyl, phenyl substituted by heterocyclyl, phenyl substituted by heteroaryl, phenyl substituted by —O-cycloalkyl or phenyl substituted by -cycloalkyl-heterocyclyl; and in which any of aforesaid aryl, cycloalkyl, heterocyclyl, heteroaryl, phenyl or phenoxy groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl)($C_{1-4}$alkyl), —$C(O)N(C_{1-4}$alkyl)($C_{1-4}$alkyl), —$C(O)NH_2$, —$C(O)NH(C_{1-4}$alkyl) and —C(O)NH($C_{3-10}$cycloalkyl); $R^2$ represents —$C_{1-6}$alkyl, $C_{1-6}$haloalkyl, -aryl, —$C_{1-6}$alkylaryl, -cycloalkyl, —$C_{1-6}$alkylcycloalkyl, -heteroaryl, —$C_{1-6}$alkylheteroaryl, -heterocyclyl or —$C_{1-6}$alkylheterocyclyl; and in which any of aforesaid aryl, heteroaryl or heterocyclyl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl)($C_{1-4}$alkyl), —C(O) $N(C_{1-4}$alkyl)($C_{1-4}$alkyl), —$C(O)NH_2$, —C(O)NH ($C_{1-4}$alkyl) and —C(O)NH($C_{3-10}$cycloalkyl); $R^3$ represents $C_{1-6}$alkyl or $C_{1-6}$haloalkyl; n represents an integer selected from 0 to 3; and $R^a$ represents $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl)($C_{1-4}$alkyl), —$C(O)N(C_{1-4}$alkyl)($C_{1-4}$alkyl), —$C(O)NH_2$, —$C(O)NH(C_{1-4}$alkyl) and —C(O)NH($C_{3-10}$cycloalkyl).

The present teachings include radiolabeled glutaminylcyclase (QC) inhibitor compounds of formula $(I)^a$:

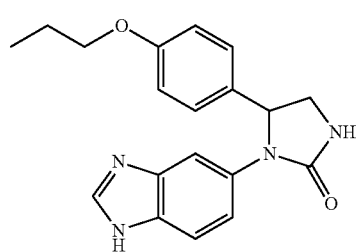

(I)$^a$

In some embodiments, the radiolabeled compound is of formula $(II)^a$:

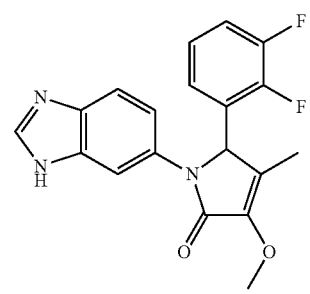

(II)$^a$

The present teachings include radiolabeled glutaminylcyclase (QC) inhibitor compounds of formula (III):

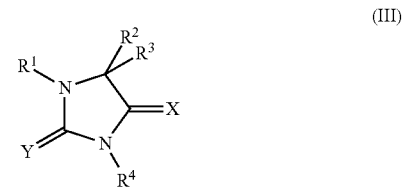

(III)

or a pharmaceutically acceptable salt, solvate or polymorph thereof, including all tautomers and stereoisomers thereof wherein: $R^1$ represents —$C_{3-8}$carbocyclyl-heteroaryl, —$C_{2-8}$alkenylheteroaryl, —$C_{1-6}$alkylheteroaryl, or $(CH_2)_aCR^5R^6(CH_2)_b$heteroaryl wherein a and b independently represent integers 0-5 provided that a+b=0-5 and $R^5$ and $R^6$ are alkylene which, together with the carbon to which they are attached, form a $C_3$-$C_5$cycloalkyl group, or a bicyclic heteroaryl group; in which any of aforesaid heteroaryl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl)($C_{1-4}$alkyl), —$C(O)N(C_{1-4}$alkyl)($C_{1-4}$alkyl), —$C(O)NH_2$, —$C(O)NH(C_{1-4}$alkyl) and —C(O)NH ($C_{3-10}$cycloalkyl); and in which any of aforesaid carbocyclyl groups may optionally be substituted by one or more groups selected from $C_{1-4}$alkyl, oxo, halogen and $C_{1-4}$alkoxy; $R^2$ represents $C_{1-8}$alkyl, aryl, heteroaryl, carbocyclyl, heterocyclyl, —$C_{1-4}$alkylaryl, —$C_{1-4}$alkylheteroaryl, —$C_{1-4}$alkylcarbocyclyl or —$C_{1-4}$alkylheterocyclyl; in which any of aforesaid aryl and heteroaryl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)OC_{1-6}$alkyl, $C_{1-6}$alkoxy-$C_{1-6}$alkyl-, nitro, halogen, cyano, hydroxyl, —C(O)OH, —$NH_2$, —$NHC_{1-4}$alkyl, —$N(C_{1-4}$alkyl)($C_{1-4}$alkyl), —C(O) $N(C_{1-4}$alkyl)($C_{1-4}$alkyl), —$C(O)NH_2$, —C(O)NH ($C_{1-4}$alkyl) and —C(O)NH($C_{3-10}$cycloalkyl); and in which any of aforesaid carbocyclyl and heterocyclyl groups may optionally be substituted by one or more groups selected from $C_{1-4}$alkyl, oxo, halogen and $C_{1-4}$alkoxy; or $R^2$ represents phenyl substituted by phenyl, phenyl substituted by a monocyclic heteroaryl group, phenyl substituted by benzyloxy, phenyl fused to carbocyclyl, phenyl fused to heterocyclyl, —C$_{1-4}$alkyl(phenyl substituted by phenyl), —C$_{1-4}$alkyl(phenyl substituted by a monocyclic heteroaryl group), —C$_{1-4}$alkyl(phenyl substituted by benzyloxy), —C$_{1-4}$alkyl(optionally substituted phenyl fused to optionally substituted carbocyclyl or —C$_{1-4}$alkyl(optionally substituted phenyl fused to optionally substituted heterocyclyl); in which any of aforesaid phenyl, benzyloxy and heteroaryl groups may optionally be substituted by one or more groups selected from C$_{1-4}$alkyl, halogen and C$_{1-4}$alkoxy, and in which any of aforesaid carbocyclyl and heterocyclyl groups may optionally be substituted by one or more groups selected from C$_{1-4}$alkyl, oxo, halogen and C$_{1-4}$alkoxy; R$^3$ represents H, —C$_{1-4}$alkyl or aryl; in which aforesaid aryl may optionally be substituted by one or more groups selected from C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, —SO$_2$C$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-8}$alkynyloxy-, —C(O)C$_{1-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and, —C(O)NH(C$_{3-10}$cycloalkyl); or R$^2$ and R$^3$ are joined to form a carbocyclyl ring which is optionally substituted by one or more C$_{1-2}$alkyl groups; or R$^2$ and R$^3$ are joined to form a carbocyclyl ring which is fused to phenyl, wherein aforesaid carbocyclyl and/or phenyl may optionally be substituted by one or more groups selected from C$_{1-4}$alkyl, halogen and C$_{1-4}$alkoxy; or R$^2$ and R$^3$ are joined to form a carbocyclyl ring which is fused to monocyclic heteroaryl, wherein aforesaid carbocyclyl and/or heteroaryl may optionally be substituted by one or more groups selected from C$_{1-4}$alkyl, halogen and C$_{1-4}$alkoxy; R$^4$ represents H, —C$_{1-8}$alkyl, —C(O)C$_{1-6}$alkyl or —NH$_2$; X represents O or S; and Y represents O or S.

In some embodiments, a compound of the present disclosure comprises a single radiolabel. In some embodiments, the radiolabel is selected from the group consisting of $^2$H (D or deuterium), $^3$H (T or tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. In some embodiments, the radiolabel is selected from the group consisting of $^{11}$C, $^{13}$C $^{18}$F, $^{19}$F, $^{120}$I, $^{123}$I, $^{131}$I, $^{75}$Br and $^{76}$Br. In some embodiments, the radiolabel is $^{11}$C. In some embodiments, the radiolabel is $^{14}$C. In some embodiments, the radiolabel is $^{13}$C.

In some embodiments, the radiolabel is $^{11}$C and the radiolabeled compound is a compound of formula (IV):

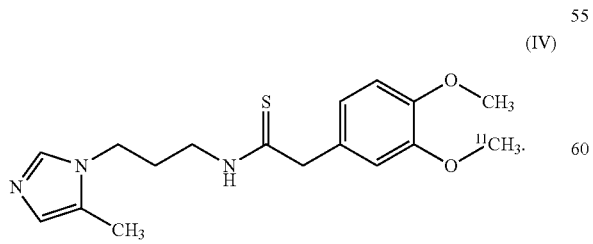

(IV)

In some embodiments, the radiolabel is $^{11}$C and the radiolabeled compound is a compound of formula (V):

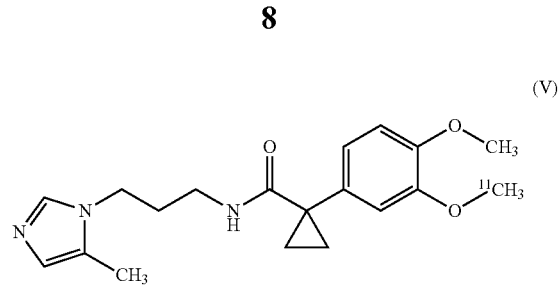

(V)

In some embodiments, the radiolabel is $^{11}$C and the radiolabeled compound is a compound of formula (I)$^d$:

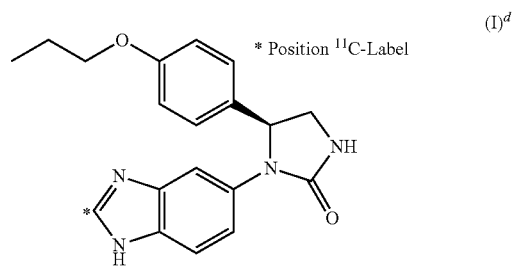 [SMILES: CCCOc1ccc([C@H]2CNC(=O)N2c2ccc3[nH]cnc3c2)cc1]

(I)$^d$

In some embodiments, the radiolabel is $^{14}$C and the radiolabeled compound is a compound of formula (I)$^c$:

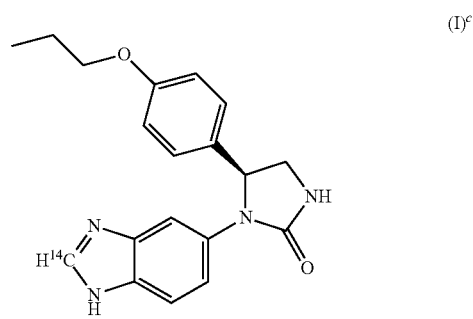 [SMILES: CCCOc1ccc([C@H]2CNC(=O)N2c2ccc3[nH][14cH]nc3c2)cc1]

(I)$^c$

In some embodiments, the radiolabel is $^{14}$C and the radiolabeled compound is a compound of formula (II)$^c$:

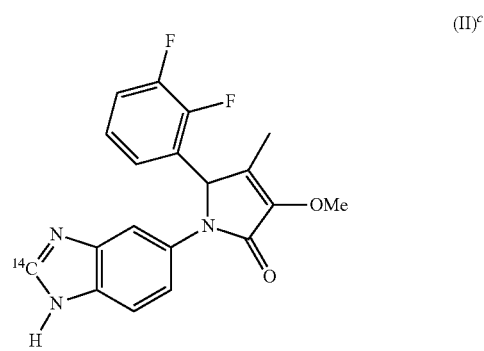 [SMILES: COC1=C(C)C(c2cccc(F)c2F)N(c2ccc3[nH][14cH]nc3c2)C1=O]

(II)$^c$

In some embodiments, the radiolabel is $^{14}$C and the radiolabeled compound is a compound of formula (II)$^d$:

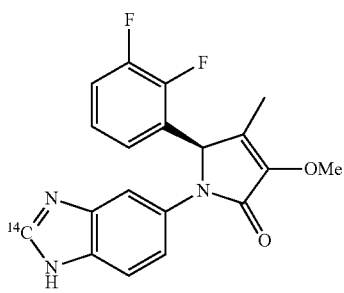

In some embodiments, the radiolabel is $^{13}C$ and the radiolabeled compound is a compound of formula (I)$^e$:

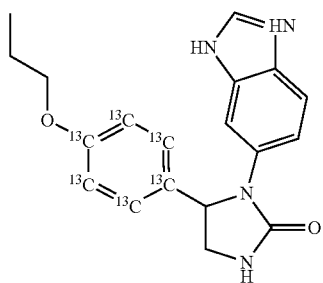

In some embodiments, the radiolabel is $^{13}C$ and the radiolabeled compound is a compound of formula (I)$^f$:

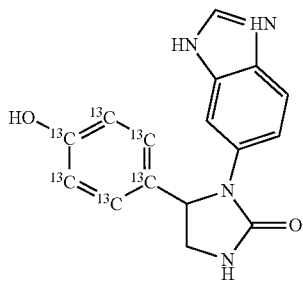

In some embodiments, the radiolabeled compound is used as an imaging agent in the detection of a neurological disorder.

The present teachings include a pharmaceutical composition comprising a radiolabeled compound as described herein or a pharmaceutically acceptable salt, solvate or polymorph thereof, including all tautomers and stereoisomers thereof, in combination with one or more pharmaceutically acceptable excipients. In some embodiments, the pharmaceutical composition is for use as an imaging agent in the detection of a neurological disorder. In some embodiments, the pharmaceutical composition is for use as an imaging agent in the detection of a neurological disorder selected from mild cognitive impairment, Alzheimer's disease, Familial British Dementia, Familial Danish Dementia, neurodegeneration in Down Syndrome and Huntington's disease, such as Alzheimer's disease.

In some embodiments, the radiolabeled compound or pharmaceutical composition is for use in the detection of amyloid peptides. In some embodiments, the radiolabeled compound or pharmaceutical composition is for use in the detection of tau proteins of neurofibrillary tangles.

The present teachings include a method for imaging and detection of senile plaques and/or neurofibrillary tangles in a brain tissue, the method comprising treating the tissue with an radiolabeled inhibitor compound as described herein for detection of neurological disorders. In some embodiments, the neurological disorder is detected by measuring the affinity of an inhibitor as described herein for senile plaques. In some embodiments, the neurological disorder is detected by measuring the affinity of an inhibitor as described herein for tau aggregates.

The present teachings include a method for ex vivo or in vitro detection of amyloid deposits in a brain tissue, the method comprising treating the tissue with a radiolabeled inhibitor compound as described herein for detection of the amyloid deposit.

The present teachings include a method for in vivo detection of amyloid deposits in a patient, the method comprising administering an effective amount of a radiolabeled inhibitor compound as described herein to the patient, and detecting the binding level of the compound to the amyloid deposit to the patient.

The present teachings include a method for ex vivo or in vitro detection of tau proteins in a brain tissue, the method comprising treating the tissue with a radiolabeled inhibitor compound as described herein for detection of the neurofibrillary tangles.

The present teachings include a method for in vivo detection of neurofibrillary tangles in a patient, the method comprising administering an effective amount of a radiolabeled inhibitor compound as described herein to the patient, and detecting the binding level of the compound to tau proteins.

In some embodiments of the methods described herein, detection is performed using gamma imaging, magnetic resonance imaging, magnetic resonance spectroscopy or fluorescence spectroscopy. In some embodiments the detection by gamma imaging is PET or SPECT.

The present teachings include a kit for diagnosing a neurological disorder which comprises a pharmaceutical composition as described herein and instructions to use said kit in accordance with the methods described herein. In some embodiments of the kit, the neurological disorder is mild cognitive impairment, Alzheimer's disease, Familial British Dementia, Familial Danish Dementia, neurodegeneration in Down Syndrome and Huntington's disease, such as Alzheimer's disease.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1:
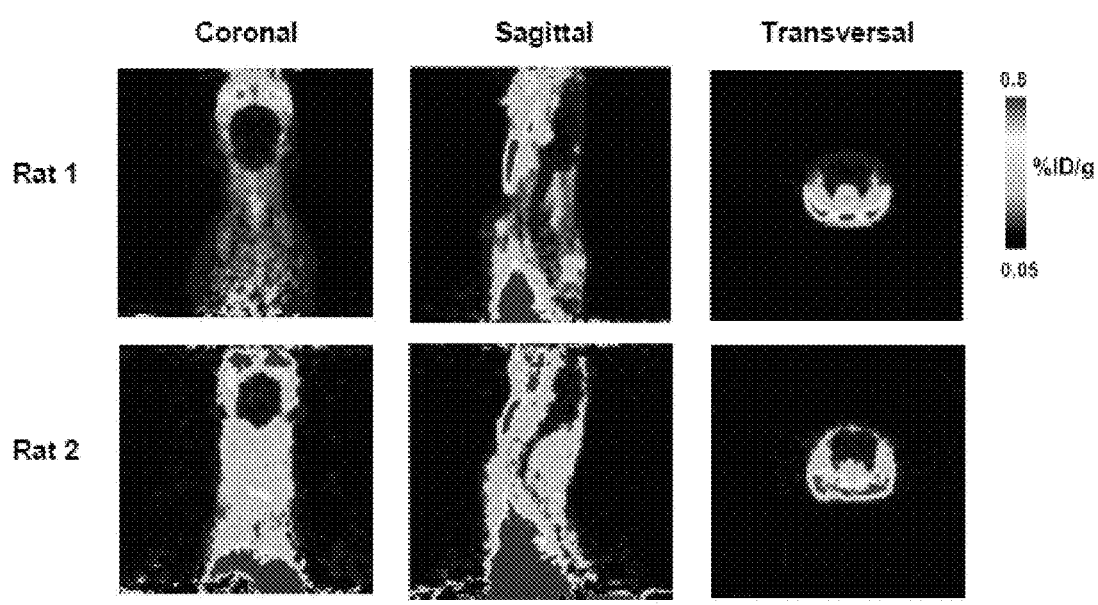
FIG. 1 shows the PET summation images (0-60 min) after administration of compound (I)$^d$ in two rats.

According to a first aspect of the present disclosure, there is provided a radiolabeled glutaminyl cyclase (QC) inhibitor for use as an imaging agent.

References herein to "radiolabeled" include a compound where one or more atoms are replaced or substituted by an atom having an atomic mass or mass number different from the atomic mass or mass number typically found in nature (i.e., naturally occurring). One non-limiting exception is $^{19}$F, which allows detection of a molecule which contains this element without enrichment to a higher degree than what is naturally occurring. Compounds carrying the substituent $^{19}$F may thus also be referred to as "labelled" or the like. The term radiolabeled may be interchangeably used with "isotopically-labelled", "labelled", "isotopic tracer group" "isotopic marker", "isotopic label", "detectable isotope" or "radioligand".

In one embodiment, the glutaminyl cyclase (QC) inhibitor comprises a single radiolabeled group.

Examples of suitable, non-limiting radiolabel groups include: $^2$H (D or deuterium), $^3$H (T or tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. It is to be understood that an isotopically labeled compound needs only to be enriched with a detectable isotope to, or above, the degree which allows detection with a technique suitable for the particular application, e.g. in a detectable compound labeled with $^{11}$C, the carbon-atom of the labeled group of the labeled compound may be constituted by $^{12}$C or other carbon-isotopes in a fraction of the molecules. The radionuclide that is incorporated in the radiolabeled compounds will depend on the specific application of that radiolabeled compound. For example, for in vitro plaque or receptor labelling and in competition assays, compounds that incorporate $^3$H, $^{14}$C, or $^{125}$I will generally be most useful. For in vivo imaging applications $^{11}$C, $^{13}$C, $^{18}$F, $^{19}$F, $^{120}$I, $^{123}$I, $^{131}$I, $^{75}$Br, or $^{76}$Br will generally be most useful. In one embodiment, the radiolabel is $^{11}$C. In an alternative embodiment, the radiolabel is $^{14}$C. In a yet further alternative embodiment, the radiolabel is $^{13}$C.

In one embodiment, the glutaminyl cyclase (QC) inhibitor is a compound of formula (I):

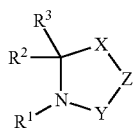

(I)

or a pharmaceutically acceptable salt, solvate or polymorph thereof, including all tautomers and stereoisomers thereof wherein:

$R^1$ represents heteroaryl, -carbocyclyl-heteroaryl, —$C_{2-6}$alkenylheteroaryl, —$C_{1-6}$alkylheteroaryl, or $(CH_2)_aCR^5R^6(CH_2)_b$heteroaryl wherein a and b independently represent integers 0-5 provided that a+b=0-5 and $R^5$ and $R^6$ are alkylene which together with the carbon to which they are attached form a $C_3$-$C_5$ cycloalkyl group;

in which any of aforesaid heteroaryl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —SO$C_{1-4}$alkyl, —SO$_2C_{1-4}$alkyl, $C_{1-6}$alkoxy-, —O—$C_{3-8}$cycloalkyl, $C_{3-8}$cycloalkyl, —SO$_2C_{3-8}$cycloalkyl, —SO$C_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —NH$_2$, —NH$C_{1-4}$alkyl, —N($C_{1-4}$alkyl)($C_{1-4}$alkyl), —C(O)N($C_{1-4}$alkyl)($C_{1-4}$alkyl), —C(O)NH$_2$, —C(O)NH($C_{1-4}$alkyl) and —C(O)NH($C_{3-10}$cycloalkyl);

and in which any of aforesaid carbocyclyl groups may optionally be substituted by one or more groups selected from $C_{1-4}$alkyl, oxo, halogen and $C_{1-4}$alkoxy;

$R^2$ represents H, $C_{1-8}$alkyl, aryl, heteroaryl, carbocyclyl, heterocyclyl, —$C_{1-4}$alkylaryl, —$C_{1-4}$alkylheteroaryl, —$C_{1-4}$alkylcarbocyclyl or —$C_{1-4}$alkylheterocyclyl;

in which any of aforesaid aryl and heteroaryl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —SO$C_{1-4}$alkyl, —SO$_2C_{1-4}$alkyl, $C_{1-6}$alkoxy-, —O—$C_{3-8}$cycloalkyl, $C_{3-8}$cycloalkyl, —SO$_2C_{3-8}$cycloalkyl, —SO$C_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, $C_{1-6}$alkoxy-$C_{1-6}$alkoxy-, nitro, halogen, halo$C_{1-6}$alkyl, halo$C_1$ 6 alkoxy, cyano, hydroxyl, —C(O)OH, —NH$_2$, —NH$C_{1-4}$alkyl, —N($C_{1-4}$alkyl)($C_{1-4}$alkyl), —N($C_{1-4}$alkyl)($C_{1-4}$alkyl)-N($C_{1-4}$alkyl)($C_{1-4}$alkyl), —$C_{1-4}$alkyl-N($C_{1-4}$alkyl)($C_{1-4}$alkyl), —$C_{1-4}$alkoxy-N($C_{1-4}$alkyl)($C_{1-4}$alkyl), —N($C_{3-8}$cycloalkyl)($C_{3-8}$cycloalkyl), —N(—$C_{1-6}$alkyl-$C_{1-6}$alkoxy)(—$C_{1-6}$alkyl-$C_{1-6}$alkoxy), —C(O)N($C_{1-4}$alkyl)($C_{1-4}$alkyl), —C(O)NH$_2$, —C(O)NH($C_{1-4}$alkyl) and —C(O)N H($C_{3-10}$cycloalkyl);

and in which any of aforesaid carbocyclyl and heterocyclyl groups may optionally be substituted by one or more groups selected from $C_{1-4}$alkyl, oxo, halogen, —C(O)$C_{1-6}$alkyl and $C_{1-4}$alkoxy;

or $R^2$ represents phenyl substituted by phenyl, phenyl substituted by a monocyclic heteroaryl group, phenyl substituted by phenoxy, phenyl substituted by heterocyclyl, phenyl substituted by heterocyclyl wherein said heterocyclyl is substituted by phenyl, phenyl substituted by —O—$C_{1-4}$alkyl-heterocyclyl, phenyl substituted by benzyloxy, phenyl substituted by carbocyclyl, phenyl substituted by carbocyclyl wherein said carbocyclyl is substituted by heterocyclyl, phenyl substituted by —O-carbocyclyl, heterocyclyl substituted by phenyl, carbocyclyl substituted by phenyl, phenyl fused to carbocyclyl, phenyl fused to heterocyclyl, —$C_{1-4}$alkyl(phenyl substituted by phenyl), —$C_{1-4}$alkyl(phenyl substituted by a monocyclic heteroaryl group), —$C_{1-4}$alkyl(phenyl substituted by a monocyclic heterocyclyl group), —$C_{1-4}$alkyl(phenyl substituted by an —O-carbocyclyl group), —$C_{1-4}$alkyl(phenyl substituted by benzyloxy), —$C_{1-4}$alkyl(optionally substituted phenyl fused to optionally substituted carbocyclyl or —$C_{1-4}$alkyl(optionally substituted phenyl fused to optionally substituted heterocyclyl);

in which any of aforesaid phenyl, benzyloxy and heteroaryl groups may optionally be substituted by one or more groups selected from $C_{1-4}$alkyl, halogen and $C_{1-4}$alkoxy, and in which any of aforesaid carbocyclyl and heterocyclyl groups may optionally be substituted by one or more groups selected from methyl, phenyl, oxo, halogen, hydroxyl and $C_{1-4}$alkoxy;

$R^3$ represents H, —$C_{1-4}$alkyl or aryl;

in which aforesaid aryl may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —SO$C_{1-4}$alkyl, —SO$_2C_{1-4}$alkyl, $C_{1-6}$alkoxy-, —O—$C_{3-8}$cycloalkyl, $C_{3-8}$cycloalkyl, —SO$_2C_{3-8}$cycloalkyl, —SO$C_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —NH$_2$, —NH$C_{1-4}$alkyl, —N($C_{1-4}$alkyl)

(C₁₋₄alkyl), —C(O)N(C₁₋₄alkyl)(C₁₋₄alkyl), —C(O)NH₂, —C(O)NH(C₁₋₄alkyl) and, —C(O)NH(C₃₋₁₀cycloalkyl);

or R² and R³ are joined to form a carbocyclyl ring which is optionally substituted by one or more C₁₋₂alkyl groups;

or R² and R³ are joined to form a carbocyclyl ring which is fused to phenyl, wherein aforesaid carbocyclyl and/or phenyl may optionally be substituted by one or more groups selected from C₁₋₄alkyl, halogen and C₁₋₄alkoxy;

or R² and R³ are joined to form a carbocyclyl ring which is fused to monocyclic heteroaryl, wherein aforesaid carbocyclyl and/or heteroaryl may optionally be substituted by one or more groups selected from C₁₋₄alkyl, halogen and C₁₋₄alkoxy;

X represents C=O, O, S, CR⁷R⁸, —O—CH₂— or —CH₂—CH₂—;

Y represents CHR⁹, C=O or C=S;

Z represents —N—R⁴, O or CHR¹⁰, such that when X represents O or S, Z must represent CHR¹⁰;

or X and Z represent two adjacent carbon atoms of a phenyl ring which is fused in that position and which is optionally substituted by one or more halogen or C₁₋₂alkyl groups;

R⁴ represents H, —C₁₋₈alkyl, —C(O)C₁₋₆alkyl or —NH₂;

R⁷ and R⁸ independently represent H, —C₁₋₄ alkyl or aryl;

in which said aforesaid aryl may be optionally substituted by C₁₋₆alkyl, C₂₋₆alkenyl, C₂₋₆alkynyl, C₁₋₆haloalkyl, —C₁₋₆thioalkyl, —SOC₁₋₄alkyl, —SO₂C₁₋₄alkyl, C₁₋₆alkoxy-, —O—C₃₋₈cycloalkyl, C₃₋₈cycloalkyl, —SO₂C₃₋₆cycloalkyl, —SOC₃₋₆cycloalkyl, C₃₋₆alkenyloxy-, C₃₋₆alkynyloxy-, —C(O)C₁₋₆alkyl, —C(O)OC₁₋₆alkyl, C₁₋₆alkoxy-C₁₋₆alkyl-, nitro, halogen, cyano, hydroxyl, —C(O)OH, —NH₂, —NHC₁₋₄alkyl, —N(C₁₋₄alkyl)(C₁₋₄alkyl), —C(O)N(C₁₋₄alkyl)(C₁₋₄alkyl), —C(O)NH₂, —C(O)NH(C₁₋₄alkyl) and, —C(O)NH(C₃₋₁₀cycloalkyl);

R⁹ and R¹⁰ independently represent H or methyl;

provided that the moiety —Y—Z—X— represents a moiety other than —C(=O)—N(—R⁴)—C(=O)— or —C(=S)—N(—R⁴)—C(=O)—.

Compounds of formula (I) are described in WO 2010/026212A1 (Probiodrug AG).

In a further embodiment, the compound of formula (I) is 1-(1H-benzo[d]imidazol-5-yl)-5-(4-propoxyphenyl)imidazolidin-2-one:

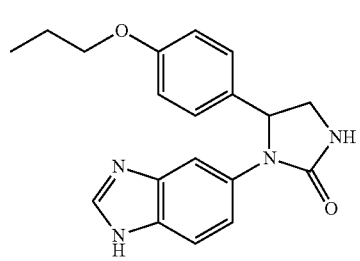

(I)ᵃ

The compound of formula (I)ᵃ is described as Example 12 in WO 2010/026212A1 (Probiodrug AG).

In a yet further embodiment, the compound of formula (I) is (S)-1-(1H-benzo[d]imidazol-5-yl)-5-(4-propoxyphenyl)imidazolidin-2-one:

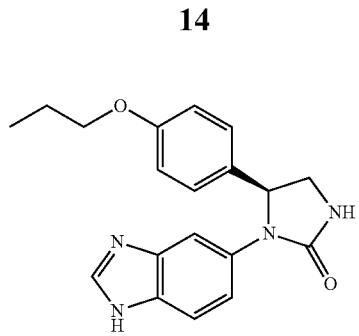

(I)ᵇ

The compound of formula (I)ᵇ is described as Example 14 in WO 2010/026212A1 (Probiodrug AG).

In one embodiment, the radiolabeled compound is a compound of formula (I)ᶜ:

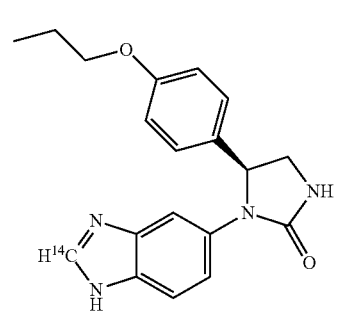

(I)ᶜ

In one embodiment, the radiolabeled compound is a compound of formula (I)ᵈ:

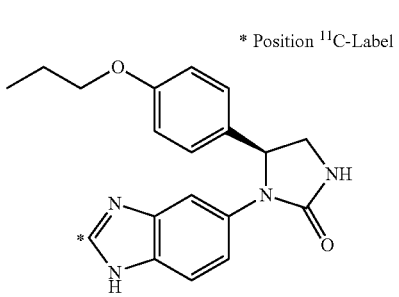

(I)ᵈ

* Position ¹¹C-Label

In one embodiment, the radiolabeled compound is a compound of formula (I)ᵉ:

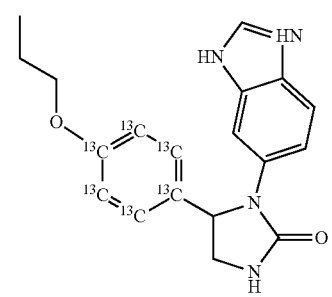

(I)ᵉ

In one embodiment, the radiolabeled compound is a compound of formula (I)ᶠ:

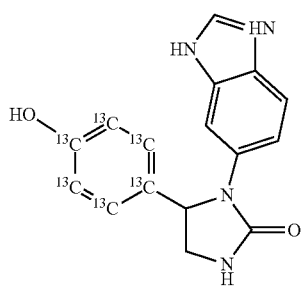
(I)ʲ

In one embodiment, the glutaminyl cyclase (QC) inhibitor is a compound of formula (II):

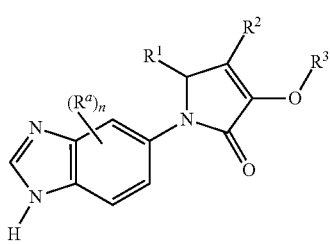
(II)

or a pharmaceutically acceptable salt, solvate or polymorph thereof, including all tautomers and stereoisomers thereof wherein:

R¹ represents —$C_{1-6}$alkyl, -aryl, —$C_{1-6}$alkylaryl, -cycloalkyl, —$C_{1-6}$alkylcycloalkyl, -heteroaryl, —$C_{1-6}$alkylheteroaryl, -heterocyclyl, —$C_{1-6}$alkylheterocyclyl, -cycloalkyl substituted by phenyl, -cycloalkyl substituted by phenoxy, -phenyl substituted by cycloalkyl, -phenyl substituted by phenoxy, -phenyl substituted by phenyl, heterocyclyl substituted by phenyl, heteroaryl substituted by phenyl, phenyl substituted by heterocyclyl, phenyl substituted by heteroaryl, phenyl substituted by —O-cycloalkyl or phenyl substituted by -cycloalkyl-heterocyclyl;

and in which any of aforesaid aryl, cycloalkyl, heterocyclyl, heteroaryl, phenyl or phenoxy groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —SO$C_{1-4}$alkyl, —SO$_2C_{1-4}$alkyl, $C_{1-6}$alkoxy-, —O—$C_{3-8}$cycloalkyl, $C_{3-8}$cycloalkyl, —SO$_2C_{3-8}$cycloalkyl, —SO$C_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —NH$_2$, —NH$C_{1-4}$alkyl, —N($C_{1-4}$alkyl)($C_{1-4}$alkyl), —C(O)N($C_{1-4}$alkyl)($C_{1-4}$alkyl), —C(O)NH$_2$, —C(O)NH($C_{1-4}$alkyl) and —C(O)NH($C_{3-10}$cycloalkyl);

R² represents —$C_{1-6}$alkyl, $C_{1-6}$haloalkyl, -aryl, —$C_{1-6}$alkylaryl, -cycloalkyl, —$C_{1-6}$alkylcycloalkyl, -heteroaryl, —$C_{1-6}$alkylheteroaryl, -heterocyclyl or —$C_{1-6}$alkylheterocyclyl;

and in which any of aforesaid aryl, heteroaryl or heterocyclyl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —SO$C_{1-4}$alkyl, —SO$_2C_{1-4}$alkyl, $C_{1-6}$alkoxy-, —O—$C_{3-8}$cycloalkyl, $C_{3-8}$cycloalkyl, —SO$_2C_{3-8}$cycloalkyl, —SO$C_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —NH$_2$, —NH$C_{1-4}$alkyl, —N($C_{1-4}$alkyl)($C_{1-4}$alkyl), —C(O)N($C_{1-4}$alkyl)($C_{1-4}$alkyl), —C(O)NH$_2$, —C(O)NH($C_{1-4}$alkyl) and —C(O)NH($C_{3-10}$cycloalkyl);

R³ represents $C_{1-6}$alkyl or $C_{1-6}$haloalkyl;

n represents an integer selected from 0 to 3; and

Rᵃ represents $C_{1-6}$alkyl, $C_{2-6}$alkenyl, $C_{2-6}$alkynyl, $C_{1-6}$haloalkyl, —$C_{1-6}$thioalkyl, —SO$C_{1-4}$alkyl, —SO$_2C_{1-4}$alkyl, $C_{1-6}$alkoxy-, —O—$C_{3-8}$cycloalkyl, $C_{3-8}$cycloalkyl, —SO$_2C_{3-8}$cycloalkyl, —SO$C_{3-6}$cycloalkyl, $C_{3-6}$alkenyloxy-, $C_{3-6}$alkynyloxy-, —C(O)$C_{1-6}$alkyl, —C(O)O$C_{1-6}$alkyl, $C_{1-6}$alkoxy-$C_{1-6}$alkyl-, nitro, halogen, cyano, hydroxyl, —C(O)OH, —NH$_2$, —NH$C_{1-4}$alkyl, —N($C_{1-4}$alkyl)($C_{1-4}$alkyl), —C(O)N($C_{1-4}$alkyl)($C_{1-4}$alkyl), —C(O)NH$_2$, —C(O)NH($C_{1-4}$alkyl) and —C(O)NH($C_{3-10}$cycloalkyl).

Compounds of formula (II) are described in WO 2011/110613A1 (Probiodrug AG).

In a further embodiment, the glutaminyl cyclase (QC) inhibitor is a compound of formula (I) or formula (II) as hereinbefore defined.

In a further embodiment, the compound of formula (II) is 1-(1H-Benzo[d]imidazol-6-yl)-5-(2,3-difluorophenyl)-3-methoxy-4-methyl-1H-pyrrol-2(5H)-one:

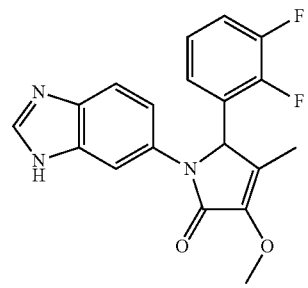
(II)ᵃ

The compound of formula (II)ᵃ is described as Example 8 in WO 2011/110613A1 (Probiodrug AG).

In a further embodiment, the compound of formula (II) is (R)-1-(1H-Benzo[d]imidazol-6-yl)-5-(2,3-difluorophenyl)-3-methoxy-4-methyl-1H-pyrrol-2(5H)-one:

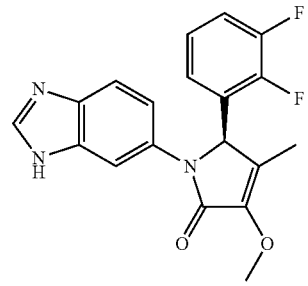
(II)ᵇ

The compound of formula (II)ᵇ is described as Example 9 in WO 2011/110613A1 (Probiodrug AG).

In one embodiment, the radiolabeled compound is a compound of formula (II)ᶜ:

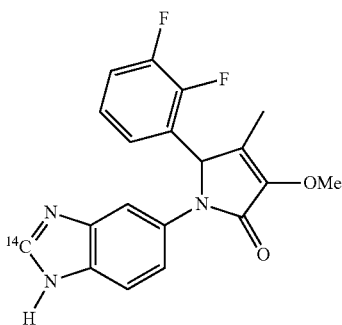

(II)$^c$

In a further embodiment, the radiolabeled compound is a compound of formula (II)$^d$:

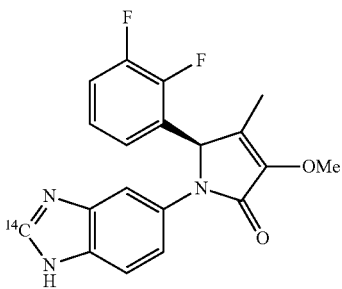

(II)$^d$

In one embodiment, the glutaminyl cyclase (QC) inhibitor is a compound of formula (III):

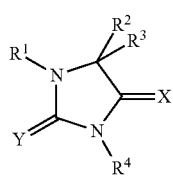

(III)

or a pharmaceutically acceptable salt, solvate or polymorph thereof, including all tautomers and stereoisomers thereof wherein:

$R^1$ represents —$C_{3-8}$carbocyclyl-heteroaryl, —$C_{2-6}$alkenyl-heteroaryl, —$C_{1-6}$alkylheteroaryl, or $(CH_2)_aCR^5R^6$ $(CH_2)_b$heteroaryl wherein a and b independently represent integers 0-5 provided that a+b=0-5 and $R^5$ and $R^6$ are alkylene which, together with the carbon to which they are attached, form a $C_3$-$C_5$ cycloalkyl group, or a bicyclic heteroaryl group;

in which any of aforesaid heteroaryl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —C(O)$C_{1-6}$alkyl, —C(O)OC$_{1-6}$alkyl, $C_{1-6}$alkoxy-$C_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl) (C$_{1-4}$alkyl), —C(O)NH$_2$, —C(O)NH(C$_{1-4}$alkyl) and —C(O)N H(C$_{3-10}$cycloalkyl);

and in which any of aforesaid carbocyclyl groups may optionally be substituted by one or more groups selected from $C_{1-4}$alkyl, oxo, halogen and $C_{1-4}$alkoxy;

$R^2$ represents $C_{1-8}$alkyl, aryl, heteroaryl, carbocyclyl, heterocyclyl, —$C_{1-4}$alkylaryl, —$C_{1-4}$alkylheteroaryl, —$C_{1-4}$alkylcarbocyclyl or —$C_{1-4}$alkylheterocyclyl;

in which any of aforesaid aryl and heteroaryl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —C(O)$C_{1-6}$alkyl, —C(O)OC$_{1-6}$alkyl, $C_{1-6}$alkoxy-$C_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and —C(O)NH (C$_{3-10}$cycloalkyl);

and in which any of aforesaid carbocyclyl and heterocyclyl groups may optionally be substituted by one or more groups selected from $C_{1-4}$alkyl, oxo, halogen and $C_{1-4}$alkoxy;

or $R^2$ represents phenyl substituted by phenyl, phenyl substituted by a monocyclic heteroaryl group, phenyl substituted by benzyloxy, phenyl fused to carbocyclyl, phenyl fused to heterocyclyl, —$C_{1-4}$alkyl(phenyl substituted by phenyl), —$C_{1-4}$alkyl(phenyl substituted by a monocyclic heteroaryl group), —$C_{1-4}$alkyl(phenyl substituted by benzyloxy), —$C_{1-4}$alkyl(optionally substituted phenyl fused to optionally substituted carbocyclyl or —$C_{1-4}$alkyl(optionally substituted phenyl fused to optionally substituted heterocyclyl);

in which any of aforesaid phenyl, benzyloxy and heteroaryl groups may optionally be substituted by one or more groups selected from $C_{1-4}$alkyl, halogen and $C_{1-4}$alkoxy, and in which any of aforesaid carbocyclyl and heterocyclyl groups may optionally be substituted by one or more groups selected from $C_{1-4}$alkyl, oxo, halogen and $C_{1-4}$alkoxy;

$R^3$ represents H, —$C_{1-4}$alkyl or aryl;

in which aforesaid aryl may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2C_{1-4}$alkyl, $C_{1-6}$alkoxy-, —O—$C_{3-8}$cycloalkyl, $C_{3-8}$cycloalkyl, —$SO_2C_{3-8}$cycloalkyl, —$SOC_{3-6}$cycloalkyl, $C_{3-6}$alkenyloxy-, $C_{3-6}$alkynyloxy-, —C(O)$C_{1-6}$alkyl, —C(O)OC$_{1-6}$alkyl, $C_{1-6}$alkoxy-$C_{1-6}$alkyl-, nitro, halogen, cyano, hydroxyl, —C(O)OH, —NH$_2$, —NHC$_{1-4}$alkyl, —N(C$_{1-4}$alkyl) (C$_{1-4}$alkyl), —C(O)N(C$_{1-4}$alkyl)(C$_{1-4}$alkyl), —C(O) NH$_2$, —C(O)NH(C$_{1-4}$alkyl) and, —C(O)NH(C$_{3-10}$cycloalkyl);

or $R^2$ and $R^3$ are joined to form a carbocyclyl ring which is optionally substituted by one or more $C_{1-2}$alkyl groups;

or $R^2$ and $R^3$ are joined to form a carbocyclyl ring which is fused to phenyl, wherein aforesaid carbocyclyl and/or phenyl may optionally be substituted by one or more groups selected from $C_{1-4}$alkyl, halogen and $C_{1-4}$alkoxy;

or $R^2$ and $R^3$ are joined to form a carbocyclyl ring which is fused to monocyclic heteroaryl, wherein aforesaid carbocyclyl and/or heteroaryl may optionally be substituted by one or more groups selected from $C_{1-4}$alkyl, halogen and $C_{1-4}$alkoxy;

$R^4$ represents H, —$C_{1-8}$alkyl, —C(O)$C_{1-6}$alkyl or —NH$_2$;

X represents O or S; and

Y represents O or S.

Compounds of formula (III) are described in GB Patent Application No. 1003936.0 (Probiodrug AG).

In one embodiment, the radiolabeled glutaminyl cyclase (QC) inhibitor is a compound of formula (IV):

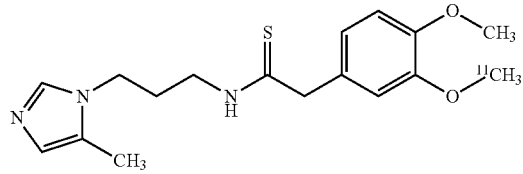

(IV)

In one embodiment, the radiolabeled glutaminyl cyclase (QC) inhibitor is a compound of formula (V):

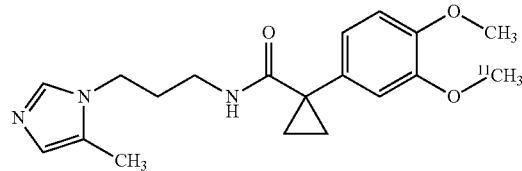

(V)

Processes for incorporating the radiolabels into the glutaminyl cyclase (QC) inhibitors may be carried out in accordance with known labelling procedures. For example, WO 2010/111303 describes the process of labelling compounds with an 18-fluorine isotope.

For example, the compound of formula (IV) may be prepared in accordance with the process shown in Scheme A:

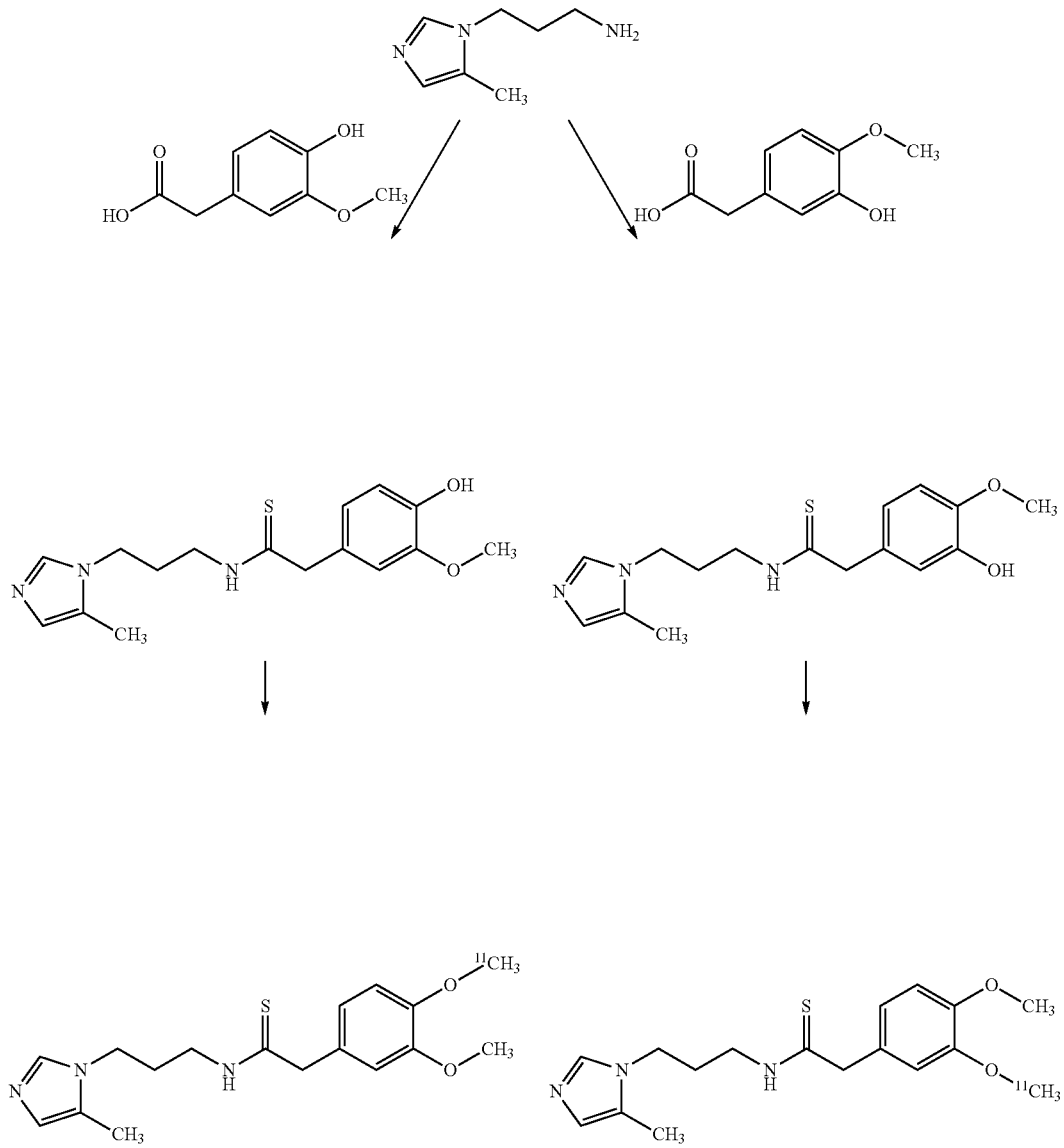

Furthermore, the compound of formula (V) may be prepared in accordance with the process shown in Scheme B:

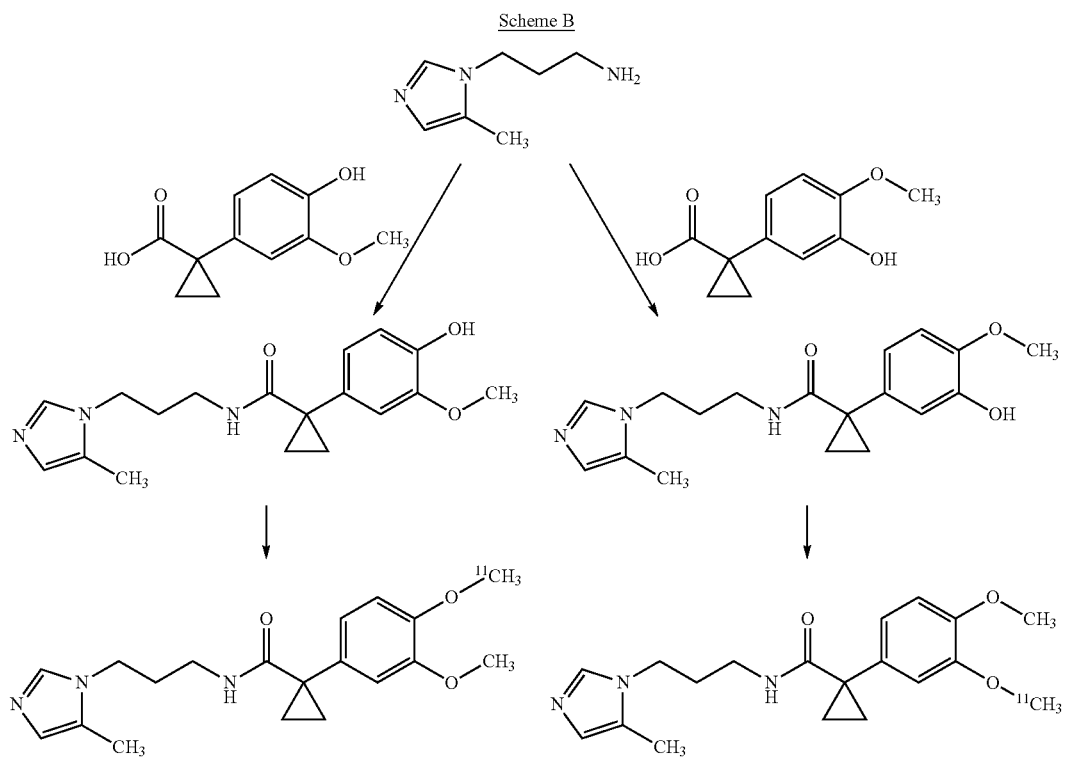

In one embodiment, the inhibitor as defined herein is used as a medical imaging agent. In a further embodiment, the inhibitor as defined herein is used as a medical imaging agent in the detection of a neurological disorder.

According to a further aspect of the present disclosure, there is provided a pharmaceutical composition comprising a radiolabeled compound as defined herein or a pharmaceutically acceptable salt, solvate or polymorph thereof, including all tautomers and stereoisomers thereof, in combination with one or more pharmaceutically acceptable excipients.

Pharmaceutically Acceptable Salts:

In view of the close relationship between the free compounds and the compounds in the form of their salts or solvates, whenever a compound is referred to in this context, a corresponding salt, solvate or polymorph is also intended, provided such is possible or appropriate under the circumstances.

Salts and solvates of the glutaminyl cyclase (QC) inhibitors and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present disclosure, for example, for use as intermediates in the preparation of other compounds and their pharmaceutically acceptable salts and solvates.

Suitable salts according to the present disclosure include those formed with both organic and inorganic acids or bases. Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds described herein are intended to be embraced by the scope of the present disclosure.

Polymorph Crystal Forms:

Furthermore, some of the crystalline forms of the compounds may exist as polymorphs and as such are intended to be included in the present disclosure. In addition, some of the compounds may form solvates with water (i.e. hydrates) or common organic solvents, and such solvates are also intended to be encompassed within the scope of this disclosure. The compounds, including their salts, can also be obtained in the form of their hydrates, or include other solvents used for their crystallization.

Pharmaceutically Acceptable Excipients:

Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like.

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and coloring agents.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present disclosure may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

According to a further aspect of the present disclosure, there is provided the pharmaceutical composition as defined herein, for use as an imaging agent in the detection of a neurological disorder.

Examples of suitable non-limiting neurological disorders include: mild cognitive impairment, Alzheimer's disease, Familial British Dementia, Familial Danish Dementia, neurodegeneration in Down Syndrome and Huntington's disease. In one particular embodiment, the neurological disorder is Alzheimer's disease.

In one embodiment, the inhibitor or composition of the present disclosure is used in the detection of amyloid peptides.

In one embodiment, the inhibitor or composition of the present disclosure is used in the detection of tau proteins of neurofibrillary tangles.

The detection of such amyloid peptides has utility in the detection and quantification of amyloid deposits and/or neurofibrillary tangles in diseases including, but not limited to Mediterranean fever, MuckleWells syndrome, idiopathetic myeloma, amyloid polyneuropathy, amyloid cardiomyopathy, systemic senile myloidosis, amyloid polyneuropathy, hereditary cerebral hemorrhage with amyloidosis, Down's syndrome, Scrapie, Creutzfeldt-Jacob disease, Kuru, Gerstamnn-Straussler-Scheinker syndrome, medullary carcinoma of the thyroid, Isolated atrial amyloid, [beta] 2-microglobulin amyloid in dialysis patients, inclusionbody myositis, β2-amyloiddeposits in muscle wasting disease, chronic traumatic encephalopathy (CTE), and Islets of Langerhans diabetes Type II insulinoma.

The radiolabeled compounds of the present disclosure may be administered by any means known to the person skilled in the art. For example, administration may be local or systemic and accomplished orally, parenterally, by inhalation spray, topically, rectally, inhaled, nasally, buccally, vaginally, or via an implanted reservoir. The term "parenteral" as used herein includes subcutaneous, intravenous, intraarterial, intramuscular, intraperitoneal, intrathecal, intraventricular, intrasternal, intracranial, and intraosseous injection and infusion techniques.

Dose levels can range from about 0.001 μg/kg/day to about 10,000 mg/kg/day. In one embodiment, the dose level is about 0.001 μg/kg/day to about 10 g/kg/day. In another embodiment, the dose level is about 0.01 μg/kg/day to about 1.0 g/kg/day. In yet another embodiment, the dose level is about 0.1 mg/kg/day to about 100 mg/kg/day.

The exact administration protocol and dose levels will vary depending upon various factors including the age, body weight, general health, sex and diet of the patient; the determination of specific administration procedures would be routine to any one of ordinary skill in the art.

The regimen may include pre-treatment and/or co-administration with additional compounds such as for example therapeutic agent(s).

According to a further aspect of the present disclosure there is provided a method for imaging and detection of senile plaques and/or neurofibrillary tangles in a brain tissue, the method comprising treating the tissue with an inhibitor as defined herein for detection of neurological disorders.

In one embodiment, the neurological disorder is detected by measuring the affinity of an inhibitor as defined herein for senile plaques.

In one embodiment, the neurological disorder is detected by measuring the affinity of an inhibitor as defined herein for tau aggregates.

According to a further aspect of the present disclosure there is provided a method for ex vivo or in vitro detection of amyloid deposits in a brain tissue, the method comprising treating the tissue with an inhibitor as defined herein for detection of the amyloid deposit.

According to a further aspect of the present disclosure there is provided a method for in vivo detection of amyloid deposits in a patient, the method comprising administering an effective amount of an inhibitor as defined herein to the patient, and detecting the binding level of the compound to the amyloid deposit to the patient.

According to a further aspect of the present disclosure there is provided a method for ex vivo or in vitro detection of tau proteins in a brain tissue, the method comprising treating the tissue with an inhibitor as defined herein for detection of the neurofibrillary tangles.

According to a further aspect of the present disclosure there is provided a method for in vivo detection of neurofibrillary tangles in a patient, the method comprising administering an effective amount of an inhibitor as defined herein to the patient, and detecting the binding level of the compound to tau proteins.

In one embodiment, the method relates to detecting senile plaques and neurofibrillary tangles characteristic for a neurological disorder.

In one embodiment, the detection is performed using gamma imaging, magnetic resonance imaging, magnetic resonance spectroscopy or fluorescence spectroscopy.

In one embodiment, the detection by gamma imaging is PET or SPECT. Positron Emission Tomography (PET) is a precise and sophisticated technique using isotopes produced in a cyclotron. A positron-emitting radionuclide is introduced, usually by injection, and accumulates in the target tissue. As it decays it emits a positron, which promptly combines with a nearby electron resulting in the simultaneous emission of two identifiable gamma rays in opposite directions. These are detected by a PET camera and give very precise indication of their origin. PET's most important clinical role is in oncology, with fluorine-18 as the tracer, since it has proven to be the most accurate non-invasive method of detecting and evaluating most cancers. It is also well used in cardiac and brain imaging.

A number of medical diagnostic procedures, including PET and SPECT utilize radiolabeled compounds, are well known in the art. PET and SPECT are very sensitive techniques and require small quantities of radiolabeled compounds, called tracers. The labeled compounds are transported, accumulated and converted in vivo in exactly the same way as the corresponding non-radioactively compound. Tracers, or probes, can be radiolabeled with a radionuclide useful for PET imaging, such as $^{11}C$, $^{13}N$, $^{15}O$, $^{18}F$, $^{64}Cu$ and $^{124}I$, or with a radionuclide useful for SPECT imaging, such as $^{99}Tc$, $^{77}Br$, $^{61}Cu$, $^{153}Gd$, $^{123}I$, $^{125}I$, $^{131}I$ and $^{32}P$.

PET creates images based on the distribution of molecular imaging tracers carrying positron-emitting isotopes in the tissue of the patient. The PET method has the potential to detect malfunction on a cellular level in the investigated tissues or organs. PET has been used in clinical oncology, such as for the imaging of tumors and metastases, and has been used for diagnosis of certain brain diseases, as well as mapping brain and heart function. Similarly, SPECT can be used to complement any gamma imaging study, where a true 3D representation can be helpful, for example, imaging tumor, infection (leukocyte), thyroid or bones.

The person skilled in the art is familiar with the various ways to detect labeled compounds for imaging purposes. For example, positron emission tomography (PET) or single photon emission computed tomography (SPECT) can be used to detect radiolabeled compounds. The label that is introduced into the compound can depend on the detection method desired. The person skilled in the art is familiar with PET detection of a positron-emitting atom, such as F. The present disclosure is also directed to specific compounds described herein where the F atom is replaced with a non-radiolabeled fluorine atom. The person skilled in the art is familiar with SPECT detection of a photon-emitting atom, such as $^{123}I$ or $^{99}Tc$.

The radiolabeled glutaminyl cyclase inhibitor of the present disclosure should typically have sufficient radioactivity and radioactivity concentration to assure reliable diagnosis. The imaging of amyloid deposits and neurofibrillary tangles can also be carried out quantitatively so that the amount of amyloid deposits and neurofibrillary tangles can be determined.

One of the key prerequisites for an in vivo imaging agent of the brain is the ability to cross the intact blood-brain barrier after a bolus i.v. injection. In the first step of the present method of imaging, the radiolabeled glutaminyl cyclase inhibitor of the present disclosure is introduced into a tissue or a patient in a detectable quantity. The compound is typically part of a pharmaceutical composition and is administered to the tissue or the patient by methods well known to those skilled in the art.

In an alternative embodiment, the radiolabeled glutaminyl cyclase inhibitor of the present disclosure is introduced into a patient in a detectable quantity and after sufficient time has passed for the compound to become associated with amyloid deposits and/or tau proteins, the labeled compound is detected non-invasively. In another embodiment of the present disclosure, a radiolabeled glutaminyl cyclase inhibitor described herein is introduced into a patient, sufficient time is allowed for the compound to become associated with amyloid deposits, and then a sample of tissue from the patient is removed and the radiolabeled compound in the tissue is detected apart from the patient. In another embodiment of the present disclosure, a tissue sample is removed from a patient and a radiolabeled glutaminyl cyclase inhibitor of the present disclosure is introduced into the tissue sample. After a sufficient amount of time for the compound to become bound to amyloid deposits and/or tau proteins, the compound is detected.

A detectable quantity is a quantity of labeled compound necessary to be detected by the detection method chosen. The amount of radiolabeled glutaminyl cyclase inhibitor of the present disclosure to be introduced into a patient in order to provide for detection can readily be determined by those skilled in the art. For example, increasing amounts of the radiolabeled compound can be given to a patient until the compound is detected by the detection method of choice. A label is introduced into the compounds to provide for detection of the compounds.

The amount of time necessary can easily be determined by introducing a detectable amount of radiolabeled glutaminyl cyclase inhibitor of the present disclosure into a patient and then detecting the radiolabeled compound at various times after administration.

According to a further aspect of the present disclosure there is provided a kit for diagnosing a neurological disorder which comprises a pharmaceutical composition as defined herein and instructions to use said kit in accordance with the methods described herein.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

Preparation of [Benzimidazole-2-$^{14}$C] Compound of Formula (I)$^b$ (Compound of (I)$^c$)

Intermediate 1

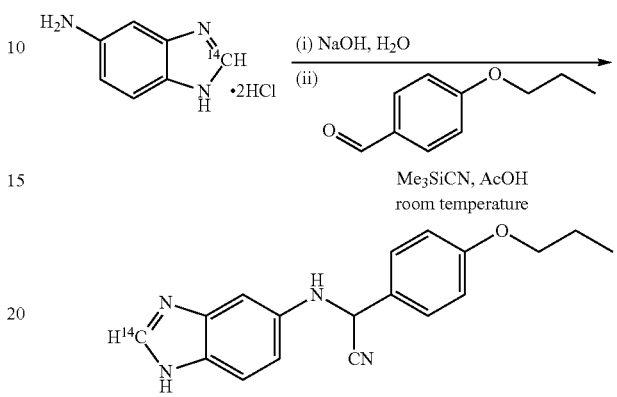

To 5-amino[2-$^{14}$C]benzimidazole dihydrochloride (1.30 g, 6.27 mmol, 375 mCi) was added water (10 ml) followed by 2 M sodium hydroxide solution (6.3 ml, 12.60 mmol). The mixture was stirred for 5 minutes at room temperature then the solvent was removed under reduced pressure. Acetic acid (6.2 ml) was added to the residue and the slurry was stirred at room temperature. Next, 4-propoxybenzaldehyde (935 mg, 5.69 mmol) was added dropwise over 15 minutes. Also, trimethylsilyl cyanide (846 mg, 8.52 mmol) was added dropwise over 15 minutes and the reaction mixture was stirred for 3 hours at room temperature under an atmosphere of nitrogen gas.

The reaction mixture was added dropwise to ice cold 28% ammonium hydroxide solution (15 ml) with stirring. The product was extracted into ethyl acetate (3×20 ml) and the extracts were combined. After drying over sodium sulphate, the slurry was filtered and the solvent was removed under reduced pressure. The product was purified by flash chromatography and the required fractions were combined. The solvent was removed under reduced pressure and the remaining solid was pumped under vacuum to constant weight to give the title compound (1.67 g, 5.22 mmol, 312 mCi).

Intermediate 2

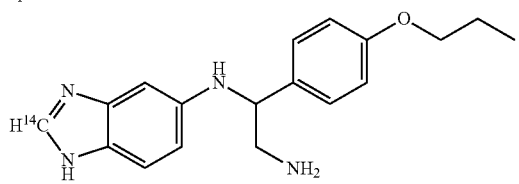

To Intermediate 1 (267 mg, 0.84 mmol, 50.0 mCi) was added a slurry of 10% palladium on carbon, Degussa type E101 R/W (51 mg) in acetic acid (3 ml) under an atmosphere of nitrogen gas. The mixture was stirred under hydrogen gas at room temperature for 18 hours.

The catalyst was removed by filtration through a pad of Celite then washed with acetic acid (10 ml). The filtrate was evaporated to dryness under reduced pressure and toluene (20 ml) was added to the residue. The solvent was removed under reduced pressure which gave the title compound (0.75 mmol, equivalent to 45 mCi).

[Benzimidazole-2-$^{14}$C] Compound of Formula (I)$^a$

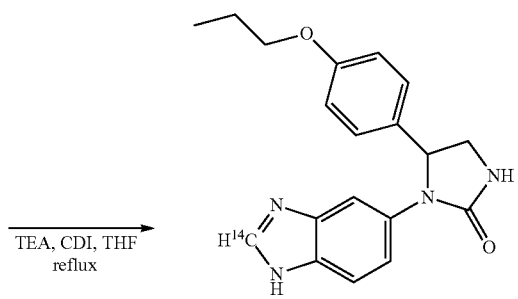 [SMILES: CCCOc1ccc(C2CNC(=O)N2c2ccc3[nH][14cH]nc3c2)cc1]

To Intermediate 2 (0.75 mmol, 45 mCi) was added tetrahydrofuran (2.8 ml), triethylamine (227 mg, 2.25 mmol) and 1,1-carbonyldiimidazole (146 mg, 0.90 mmol). The reaction mixture was stirred at 85° C. for 2 hours.

After cooling to room temperature, water (15 ml) was added and the product was extracted into ethyl acetate (3×20 ml). The extracts were combined, washed with saturated sodium chloride solution (10 ml) then dried over sodium sulfate. The slurry was filtered and the solvent was removed under reduced pressure.

The product was purified by reverse phase high performance liquid chromatography. The required fractions were combined and the organic solvent was removed under reduced pressure. To the remaining aqueous phase was added saturated sodium chloride solution (15 ml) and the product was extracted into ethyl acetate (2×15 ml). The extracts were combined and the solvent was removed under reduced pressure. This gave the title compound (0.098 mmol, equivalent to 5.9 mCi).

[Benzimidazole-2-$^{14}$C] Compound of Formula (I)$^b$

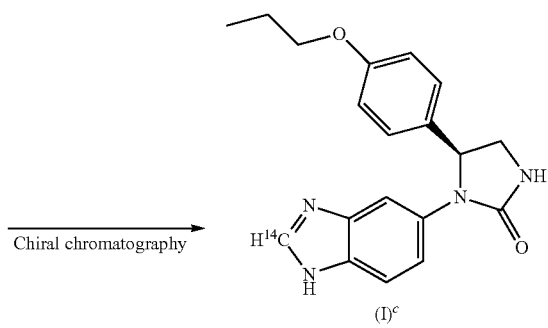

The [benzimidazole-2-$^{14}$C] Compound of Formula (I)$^a$ (0.098 mmol, equivalent to 5.9 mCi) was dissolved in n-heptane:ethanol:methanol:diethylamine (500:250:250:5; 5 ml) and the isomers were resolved by chiral high performance liquid chromatography using a Pirkle Whelk column.

The required fractions were combined and the solvent was removed under reduced pressure. The remaining residue was dissolved in acetonitrile:water (33:66; 5 ml) then lyophilised to give a solid, which was pumped to hard vacuum and constant weight. This gave the title compound (14.0 mg, 0.0415 mmol, 2.49 mCi).

Technical Data:
Specific Activity
Determined by:

| Mass Spectrometry | 61 mCi/mmol | 2.26 GBq/mmol |
| Gravimetric Analysis | 178 µCi/mg | 6.59 MBq/mg |
| Equivalent to | 60 mCi/mmol | 2.22 GBq/mmol |

Molecular Weight (at this Specific Activity): 338.3
Radiochemical Purity at HPLC: 99.9%
  Column: Phenomenex Luna C18(2) 150×4.6 mm
  Temperature: ambient
  Solvent A: 0.05% trifluoroacetic acid in water
  Solvent B: 0.05% trifluoroacetic acid in acetonitrile

| | | Time (min) | | | | |
|---|---|---|---|---|---|---|
| | | 0 | 15 | 20 | 21 | 30 |
| Gradient: | % B | 0 | 100 | 100 | 0 | 0 |

Flow Rate: 1.0 ml/min
UV Detection: 254 nm
Chemical Purity by HPLC: 99.0%
  Column: Phenomenex Luna C18(2) 150×4.6 mm
  Temperature: ambient
  Solvent A: 0.05% trifluoroacetic acid in water
  Solvent B: 0.05% trifluoroacetic acid in acetonitrile

| | | Time (min) | | | | |
|---|---|---|---|---|---|---|
| | | 0 | 15 | 20 | 21 | 30 |
| Gradient: | % B | 0 | 100 | 100 | 0 | 0 |

Flow Rate: 1.0 ml/min
UV Detection: 254 nm
Chiral Purity by HPLC: >99.9%
  Column: Regis Pirkle Whelk 02 (R,R) 250×4.6 mm 10 µm
  Temperature: ambient
  Solvent: n-heptane:ethanol:methanol:diethylamine (50:25:25:0.5)
  Gradient: Isocratic for 30 minutes
  Flow Rate: 1.0 ml/min Example 2

Preparation of [Benzimidazole-2-$^{11}$C] Compound of Formula (I)$^b$ (Compound of (I)$^d$)

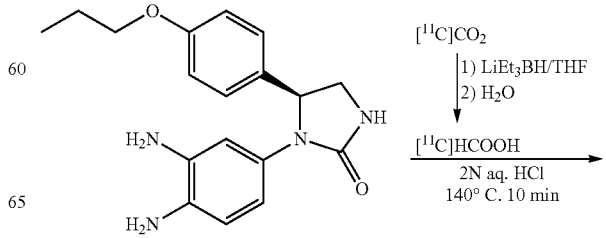

-continued

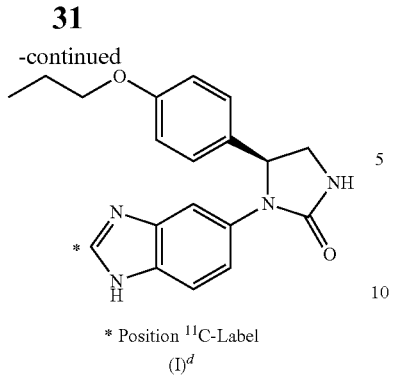

* Position ¹¹C-Label
(I)$^d$

[$^{11}$C]CO$_2$ was introduced in 100 µl THF and 50 µl LiEt$_3$BH in the reactor vessel at −20° C. After a reaction time of 40 s, hydrolysis was performed by adding 500 µl H$_2$O. As reaction product, [11$^C$]HCOOH was obtained.

Thereafter, (S)-1-(3,4-diaminophenyl)-5-(4-propoxyphenyl)imidazolidin-2-one (1 mg in 300 µl 2N aq. HCl) was added. After a reaction time of 10 min. at 140° C., the reaction mixture was cooled down and the product was purified by HPLC:
Column: Chromolith Performance RP-18 endcapped 100-4.6 mm monolithic HPLC-column (MERCK)
Solvent: 16% Acetonitrile in H$_2$O (0.1% TFA)
Flow rate: 6 ml/min
RT: (S)-1-(3,4-diaminophenyl)-5-(4-propoxyphenyl)imidazolidin-2-one: 3-7 min; compound (I)$^d$: 8-9.5 min The product peak containing compound (I)$^d$ was collected in 100 ml H$_2$O and for further purification loaded onto a SepPak tc18 column. The SepPak tc18 column was washed with 10 ml H$_2$O. Compound (I)$^d$ was then eluted with 3 ml ethanol. Thereafter the product was dried at 96° C. in an argon atmosphere.

The final tracer solution was obtained by dissolving compound (I)$^d$ in 100 µl ethanol under addition of NaCl (final concentration of ethanol max. 10%).
Specific Activity: 35.7 GBq/µmol
Stability of final tracer solution after 1.5 hours at room temperature: >98% (n=6)
Technical Data:
Analytical HPLC
HPLC: Agilent HP1200 DAD incl. Autosampler and Raytest RA detector (BGO cell)
Column: Chromolith Performance RP-18 endcapped 100-4.6 mm monolithic HPLC-column (MERCK)
Solvent: A: 0.1% TFA in H$_2$O
    B: Acetonitrile
Flow rate: 1 ml/min
Gradient: 0-10 min: 15-20% B
    10-24 min: 20-50% B
    24-26 min: 50-95% B
    26-27 min: 95% B
    27-28 min: 15% B
    28-30 min: 15% B
Equilibration: 8 min: 15% B (prior to injection)
UV Detection: 225 nm
Analytical HPLC—Chiral Method
HPLC: Agilent HP1100 DAD incl. Raytest RA Detector (PET)
Column: Chiralcel OD-H (ODH0CE-PA130) 4.6×250 mm+4.5×10 mm incl precolumn
Solvent: n-Hexane/ethanol 80/20
Flow rate: 1 ml/min
UV detection: 225 nm Example 3

Preparation of 1-(1H-Benzimidazol-5-yl)-5-(4-propoxyphenyl-[$^{13}$C$_6$]-imidazolidin-2-one (Compound of Formula (I)$^e$)

Intermediate 1: Propoxybenzene-[$^{13}$C$_6$]

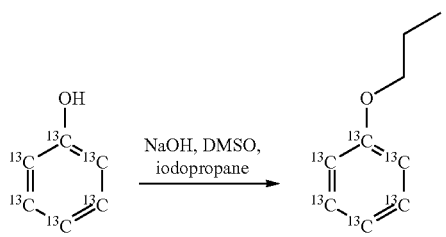

Phenol-[$^{13}$C$_6$](1.20 g, 12.0 mmol) was dissolved in DMSO (12 ml). Finely powdered sodium hydroxide (1.9 g, 48 mmol) was added, and was allowed to stir briskly at room temperature for 15 min. Iodopropane (4.08 g, 24.0 mmol) was then added dropwise over 3 min, and the reaction mixture stirred for 30 min. The reaction was sampled for a mini workup, and analysed by GC-MS. A single peak at 6.3 min (m/z 142) indicated the reaction was complete, and was worked up by addition to chilled water (100 ml). The quenched reaction was extracted with hexanes (4×25 ml), pooled and washed in succession with a dilute sodium hydroxide solution and with brine. The organic extract was dried with sodium sulphate, filtered, and solvent removed in vacuo to give a syrupy product (1.4 g, 9.9 mmol, 82%). The reaction was repeated using 1.6 g phenol-[$^{13}$C$_6$] (16 mmol) in a similar fashion to provide 1.50 g (10.6 mmol, 66%) which was combined with the above preparation. The pooled title compound was used in the subsequent step without additional purification.

Intermediate 2: 1-Bromo-4-propoxybenzene-[$^{13}$C$_6$]

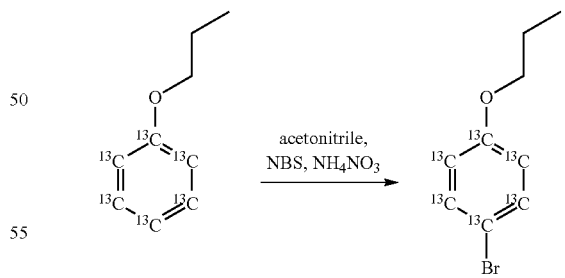

To Intermediate 1 (2.76 g, 19.4 mmol) dissolved in acetonitrile (15 ml) was added ammonium nitrate (0.15 g, 1.9 mmol, 0.1 eq, ACS grade) and stirred for 10 min. N-bromosuccinimide (3.42 g, 19.2 mmol, 0.99 eq, recrystallized from water) was added and stirred at room temperature for 30 min. Analysis by GC-MS confirmed the consumption of starting material and indicated a new product peak containing bromine at 10.8 min (m/z 220+222). The reaction was quenched in 50 ml and 50 ml hexanes. After extraction of the aqueous with additional ethyl acetate-hexanes (1:1, 4×25 ml), the pooled organic layers were washed with water followed by brine, then dried with sodium sulfate. Filtration and evaporation of solvent gave the title compound (4.2 g, 19 mmol, 98%) which was used in the subsequent step without additional purification.

Intermediate 3: 4-Propoxybenzaldehyde-[$^{13}C_6$]

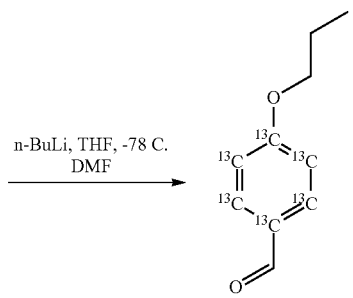

To Intermediate 2 (4.0 g, 18 mmol) in dry THF (16 ml) at −78° C. under an inert atmosphere was added n-butyllithium solution (2.5 M in hexanes, 10.9 ml, 27.1 mmol, 1.5 eq) over 5 min. This cold mixture was stirred for an additional 75 min. A solution of dry DMF (2.6 g, 36 mmol, 2 eq) in dry THF (16 ml) was then added slowly, and the reaction was stirred for 2.5 h as the cooling bath warmed to 0° C. GC-MS analysis then indicated the reaction was complete with product found at 11.5 min (m/z 170). The reaction was quenched in cold dilute citric acid and extracted with methyl tert-butylether-hexane (1:1, 4×25 ml). Pooled extracts were washed with water (2×25 ml), then brine (25 ml), and dried with sodium sulfate. Filtration and evaporation of solvent gave 3.5 g crude product. This crude product was purified on silica using ethyl acetate-hexanes (7.5:92.5) to give 2.83 g of the title compound (16.6 mmol, 92%).

Intermediate 4: [(1H-Benzimidazol-5-ylamino)]-(4-propoxyphenyl-[$^{13}C_6$])acetonitrile

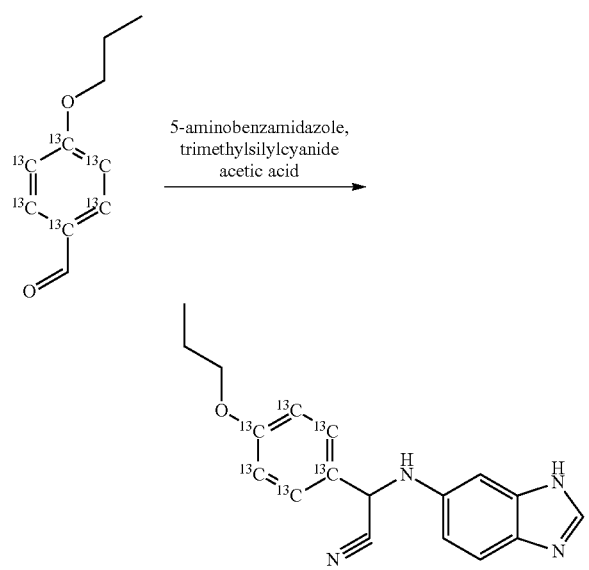

Intermediate 3 (2.0 g, 11.8 mmol) was added to a solution of 5-aminobenzimidazole (1.73 g, 13.0 mmol, 1.1 eq) in acetic acid (14 ml) and stirred for 15 min. Trimethylsilylcyanide (2.3 ml, 1.8 g, 18 mmol) was added dropwise over 15 min, and the resulting dark reaction solution was stirred for 3 h at room temperature. Reaction progress was monitored by TLC (methanol-chloroform, 10:90) and MS. Reaction mixture was quenched by addition to cold 25% ammonium hydroxide (35 ml). The resulting solid product was retained and dissolved in ethyl acetate, and the aqueous mixture was further extracted using ethyl acetate (3×25 ml). The pooled organic solutions were washed with water (2×25 ml), then brine (25 ml), dried with sodium sulfate, filtered and evaporated to give crude product which was used in the subsequent step without additional purification.

Intermediate 5: N'-(1H-Benzimidazol-5-yl)-1-(4-propoxyphenyl-[$^{13}C_6$])ethane-1,2-diamine

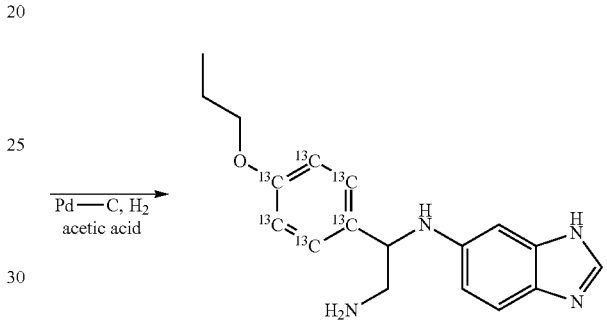

The crude product of Intermediate 4 was dissolved in acetic acid (40 ml) and was hydrogenated using Pd-carbon (10%, 0.8 g) and 40 psi hydrogen for 24 h. Filtration on celite and evaporation of solvent yielded 10 g syrupy product. TLC (methanol-chloroform 10:90, $R_f$=0) and MS(+) (m/z 317) confirmed the reaction was complete. The crude product was purified on a silica column using methanol-dichloromethane-triethylamine (2 L, 10:90:0.1), then methanol-dichloromethane-triethylamine (1.2 L, 20:80:0.1) to give 2.9 g of the title compound (9.2 mmol, 78%) over two steps.

1-(1H-Benzimidazol-5-yl)-5-yl)-5-(4-propoxyphenyl-[$^{13}C_6$]-imidazolidin-2-one (Compound of Formula (I)$^e$)

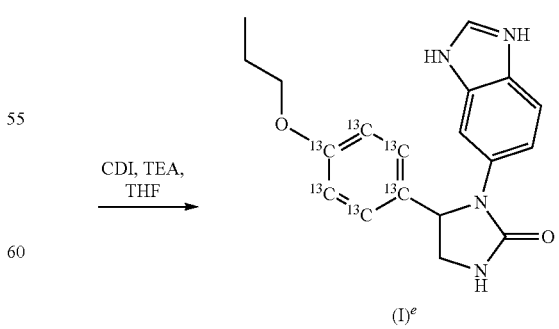

To a solution of triethylamine (1.28 g, 12.6 mmol, 4 eq) and 1,1'-carbonyldiimidazole (CDI, 0.77 g, 4.7 mmol, 1.5 eq, previously recrystallized from dry THF) in dry THF (15 ml) was added neat Intermediate 5 (1.00 g, 3.16 mmol) over 5 min. The resulting mixture was heated at 73° C. under an inert atmosphere overnight. The reaction mixture was cooled, added to water (50 ml), and extracted with ethyl acetate (4×25 ml). Pooled organic layers were washed with water (2×25 ml) and brine (25 ml), and dried with sodium sulfate. After filtration and evaporation of solvent, a syrup (0.7 g) was obtained which was purified on silica using methanol-dichloromethane (20:80). This purification gave 0.245 g of the title compound (TLC: methanol-chloroform (20:80), R$_f$=0.55, co-migrating with reference standard; MS(+) m/z 344/345), and another 0.070 g of mixture containing the title compound.

The reaction was repeated with another 1.7 g of Intermediate 5 (5.4 mmol) with the modification of using only 1.2 eq CDI (6.5 mmol). This second preparation was purified on silica using a gradient of methanol-dichloromethane (7:93 to 20:80) to give 0.376 g of tan solid title compound. As before, a mixture (0.301 g) containing desired product resulted. In each purification step, fractions containing more highly pure desired title compound were determined using HPLC (Eclipse XDB-C18, 4.6×150 mm, 3.5 μm, A=water-acetonitrile-trifluoroacetic acid (90:10:0.1), B=water-acetonitrile-trifluoroacetic acid (10:90:0.1), 0% B-100% B over 20 min, rt=9.2 min). Purity of combined product at this stage of the purification was approximately 90%. Final purification of title compound was accomplished on a column of Amberchrom CG161m (4×30 cm) using a stepwise gradient elution of water-acetonitrile (85:15, 75:25, 67:33). Fractions containing pure product were again determined using RP-HPLC. Pooled fractions were lyophilized overnight. Solid product was then redissolved in methanol-dichloromethane (5:95), and washed with half-saturated sodium bicarbonate and brine, backwashing all aqueous washes thoroughly. The organic layer was dried with sodium sulfate, filtered, and solvent evaporated using a heptane azeotrope to yield 0.317 g of the title compound (0.93 mmol).

Technical Data:
Purity by HPLC
Method: Waters Acquity with ELS detector
  Phenomenex Polar RP 4.6×150×4 μm
  A: H$_2$O
  B: MeOH

| Time (min) | % A | % B |
|---|---|---|
| 0 | 95 | 5 |
| 5 | 5 | 95 |
| 9 | 5 | 95 |

Flow: 0.6 ml/min
Result: >99%
RT: 6.43 min
Isotope Incorporation by Mass Spectrometry
Method: Agilent MSD 1100
Conditions: ES-API ionization mode
  Positive Polarity
  6 mM Ammonium Formate in Methanol:Water 7:3
Result: Molecular ion peak of 343 is consistent with expected labelling and mass spectroscopy ionization method.
Comments: The compound of (I)$^e$ has a total isotopic incorporation of >99% M+6.

Example 4

Preparation of 1-(1H-Benz[d]imidazol-5-yl)-5-(4-hydroxyphenyl-[$^{13}$C$_6$]-imidazolidin-2-one (Compound of Formula (I)$^f$)

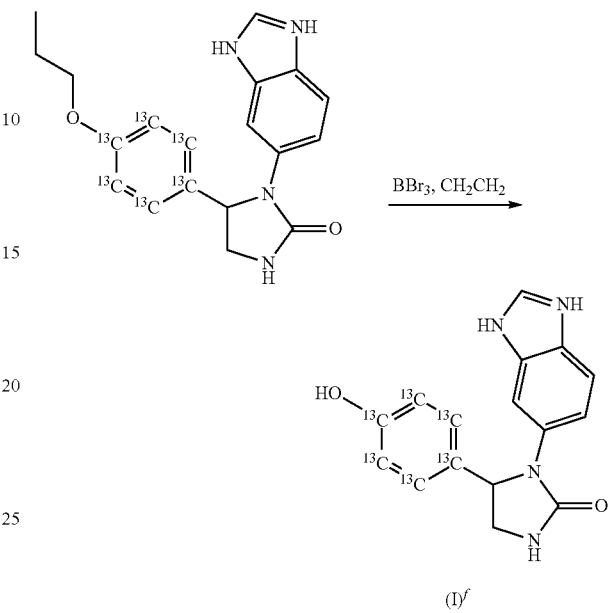

To a solution of Example 3 (0.200 g, 0.58 mmol) in dry dichloromethane at −20° C. under an inert atmosphere was added boron tribromide (0.17 ml, 0.44 g, 1.8 mmol) dropwise. An ice water cooling bath (0° C.) was then used and the reaction was stirred cold for 1 h. Using a room temperature water bath, the reaction was stirred for another 1 h. The reaction was quenched by slow addition of water (18 ml). An organic layer was reserved, and was re-extracted with more water. All clear, colorless water layers (pH~3) were combined, cooled to 5° C., and made basic by addition of 1 N sodium hydroxide. The aqueous phase was iced for 1 h, and centrifuged to give a white precipitate, which was washed with cold water, dried overnight over Drierite to give 0.138 g requiring additional purification. A column of Amberchrom CG161m (2×30 cm) using a gradient of water-acetonitrile (10:90 to 50:50). Fractions were analysed by RP-HPLC, and pooled to give two lots of the title compound (0.038 g and 0.063 g).

Technical Data:
Purity by HPLC
Method: Zorbax Bonus RP 4.6×150×5 μm
  A: H$_2$O
  B: MeOH

| Time (min) | % A | % B |
|---|---|---|
| 0 | 90 | 10 |
| 5 | 90 | 10 |
| 10 | 5 | 95 |
| 20 | 5 | 95 |

Flow: 1.0 ml/min; UV: 254 nm
Result: 97.4%
RT: 9.88 min and 9.5 min for 2 lots
Isotope Incorporation by Mass Spectrometry
Method: Agilent MSD 1100
Conditions: ES-API ionization mode
  Positive Polarity
  6 mM Ammonium Formate in Methanol:Water 7:3

Result: Molecular ion peak of 301 is consistent with expected labelling and mass spectroscopy ionization method.
Comments: The compound of (I)$^f$ has a total isotopic incorporation of >99% M+6.

Example 5

Preparation of [Benzimidazole-2-$^{14}$C] Compounds of Formulae (II)$^a$ and (II)$^b$ (Compounds of Formulae (II)$^c$ and (II)$^d$)

Intermediate 1

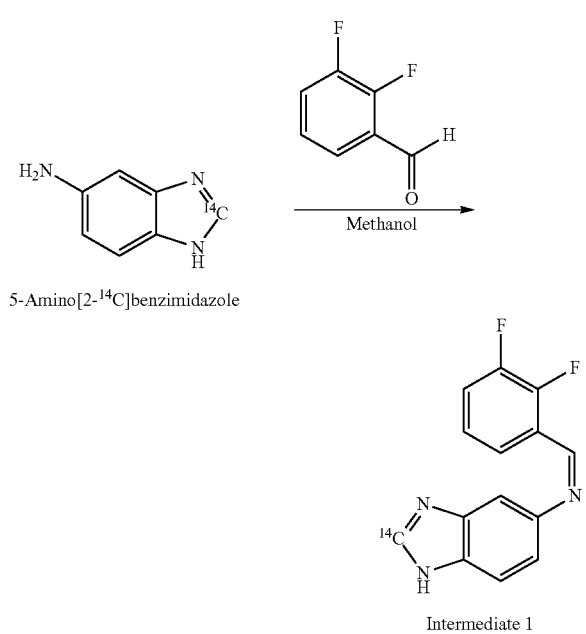

5-Amino[2-$^{14}$C]benzimidazole

To a suspension of 5-amino[2-$^{14}$C]benzimidazole.2HCl (Supplier IOI; Catalogue No. CC-544) (52.2 mCi, 60 mCi/mmol, 0.87 mmol) in methanol (2 ml) was added potassium carbonate (468 mg, 3.388 mmol) and triethylamine (236 μl, 1.694 mmol). The mixture was stirred at 0° C. for 1 hour, filtered and rotary evaporated to a brown solid. This brown solid was dissolved in methanol (1 ml) and stirred at 0° C. To this was added 2,3-difluorobenzaldehyde (119 mg, 0.837 mmol). The solution was allowed to warm to room temperature and stirred for 2 hours. The solvent was removed by rotary evaporation yielding an oil (52 mCi, 60 mCi/mmol, 0.867 mmol).

Intermediate 2

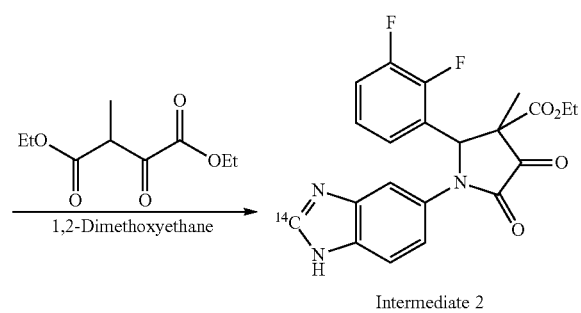 [SMILES: CCOC(=O)C(=O)C(C)C(=O)OCC ; CCOC(=O)C1(C)C(=O)C(=O)N(c2ccc3[nH][14cH]nc3c2)C1c1cccc(F)c1F]

Intermediate 2

Intermediate 1 (52 mCi, 60 mCi/mmol, 0.867 mmol) was dissolved in 1,2-dimethoxyethane (5 ml). To this was added diethyl oxalpropionate (183 μl, 0.969 mmol) and the solution was refluxed at 95° C. for 72 hours.

The product was purified by HPLC on a Gemini C18 column eluting with a 20 mM ammonium hydroxide: methanol gradient system then rotary evaporated to a solid (21.2 mCi, 60 mCi/mmol, 0.353 mmol).

Intermediate 3

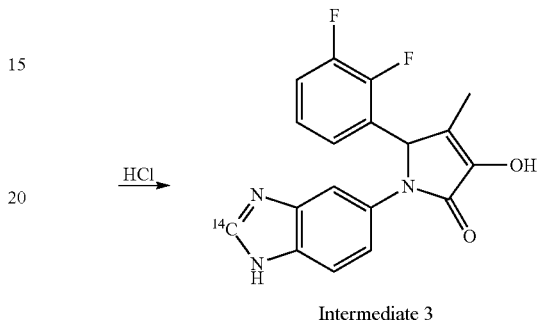

Intermediate 3

Intermediate 2 (21.2 mCi, 60 mCi/mmol, 0.353 mmol) was dissolved in concentrated hydrochloric acid (6 ml) and refluxed at 110° C. for 16 hours.

The solid was filtered, suspended in water (10 ml) and basified with saturated sodium bicarbonate to pH 8.1. Stirring was continued for 30 minutes then the mixture was filtered and rotary evaporated to a solid (16.2 mCi, 60 mCi/mmol, 0.27 mmol).

Racemic [Benzimidazole-2-$^{14}$C] Compound of Formula (II)$^a$ (Compound of Formula (II)$^c$)

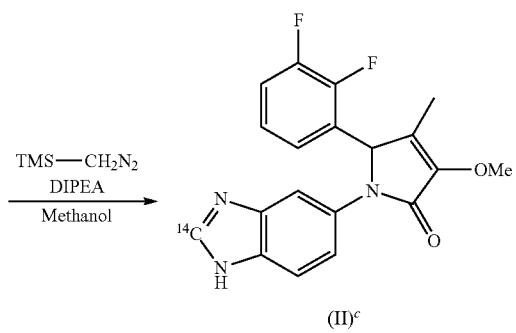

(II)$^c$

To a stirred solution of Intermediate 3 (16.2 mCi, 60 mCi/mmol, 0.27 mmol) in methanol (4 ml) was added diisopropylethylamine (53 μl, 0.303 mmol) followed by (trimethylsilyl)diazomethane (2M in ether, 275 μl, 0.55 mmol). After 15 minutes a further aliquot of (trimethylsilyl)diazomethane (275 μl, 0.55 mmol) was added and stirring was continued for 1 hour. The solvents were removed by rotary evaporation yielding a solid. The solid was then purified by HPLC on a Gemini C18 column eluting with a 20 mM ammonium hydroxide: methanol gradient system, then rotary evaporated to a solid.

Pure Isomer [Benzimidazole-2-$^{14}$C] Compound of Formula (II)$^b$ (Compound of Formula (II)$^d$)

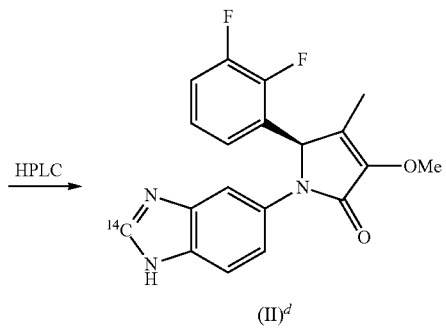 [SMILES: COC1=C(C)[C@H](c2cccc(F)c2F)N(c2ccc3[nH][14cH]nc3c2)C1=O]

(II)$^d$

The racemate compound (II)$^c$ was purified by HPLC on a Chirobiotic TAG column eluting with 40 mM ammonium acetate: methanol (4:6). The pure isomer of (II)$^c$ was freeze-dried overnight yielding a white solid (1.94 mCi, 60 mCi/mmol, 0.032 mol).

Technical Data:
Specific Activity
  Determined by:
  Mass Spectrometry: 60 mCi/mmol 2.22 GBq/mmol
Molecular Weight (at this specific activity): 357.3
Radiochemical Purity by HPLC
Column: Zorbax Bonus RP 3.5 μm (150×4.6 mm)
Solvent A: Phosphate buffer pH 6.0
Solvent B: Acetonitrile

|  | Time (min) | % A | % B |
|---|---|---|---|
| Gradient: | 0 | 100 | 0 |
|  | 2 | 100 | 0 |
|  | 20 | 10 | 90 |
|  | 21 | 100 | 0 |
|  | 30 | 100 | 0 |

Temperature: 25° C.
Flow: 1.0 ml/min
Detection: Homogeneous radiochemical detector, DAD at 225 nm
Result: 98.1%
Chiral Purity by HPLC
Column: Chirobiotic Tag 5 μm (250×4.6 mm)
Solvent A: 40 mM ammonium acetate buffer pH 4.0
Solvent B: methanol
Gradient: 60% B isocratic for 20 mins
Temperature: 20° C.
Flow Rate: 1 ml/min
Detection: Homogeneous radiochemical detector, DAD at 220 nm
Result: 98.8%

Biological Examples

Small-Animal PET Pilot Study in Rats

Two female Sprague-Dawley rats were treated with compound (I)$^d$.
Rat 1:
109.5 MBq of compound (I)$^d$ dissolved in 500 μl 0.9% NaCl/EtOH (9/1, v/v) were injected i.v. in the tail vein. The specific activity of labeled compound (I)$^d$ was 23.7 GBq/μmol. The final dose of compound (I)$^d$ administered to rat 1 was 0.009 mg/kg.
Rat 2:
29.5 MBq compound (I)$^d$ plus 0.57 mg of the unlabelled form of compound (I)$^d$ was administered i.v. in the tail vein. The final dose of compound (I)$^d$ administered to rat 2 was 3.8 mg/kg.
PET Scan
60 min dynamic PET scan of the head regions of rats 1 and 2 was performed. Blood plasma samples were taken at the end of the PET scans from retro-orbital regions. The PET summation images are shown in FIG. 1.

Figure 2:
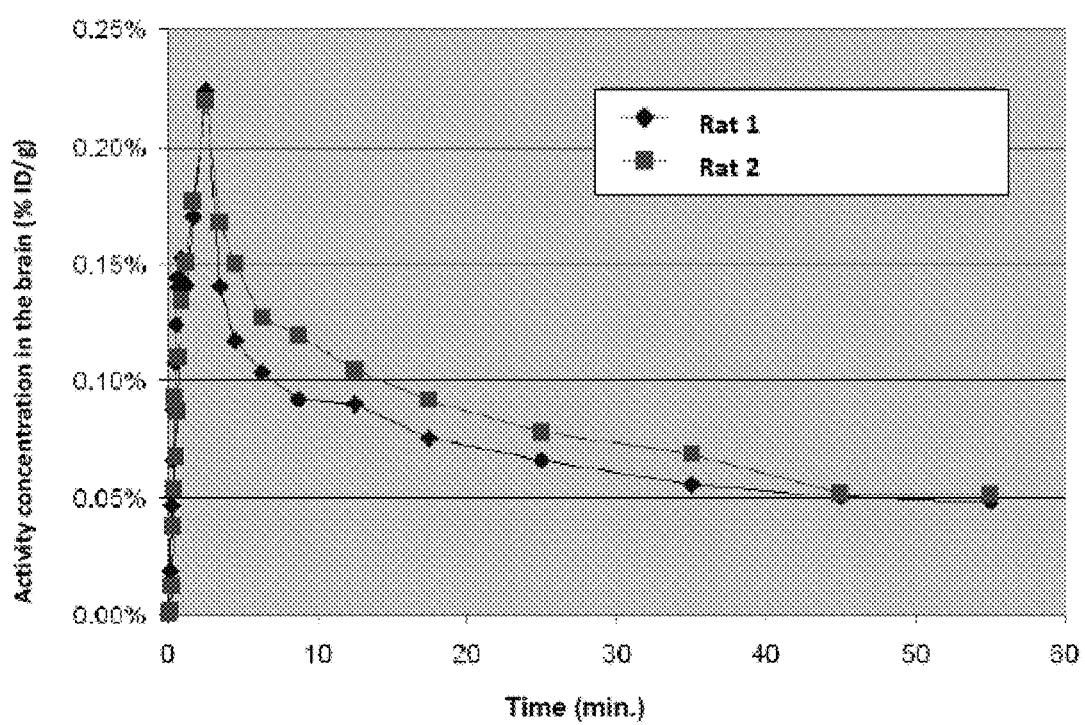
FIG. 2 shows the time-activity graphs in the brain of two rats (% administered dose per gram brain) after administration of compound (I)$^d$.

1.5 ml of the plasma samples were thoroughly mixed with 3.0 ml acetonitrile. After centrifugation, the supernatant was evaporated at 100° C. under an argon atmosphere. The dried residue was dissolved in 2 ml CH$_3$CN/0.1% aq. TFA (9/1), spiked with 20 μl unlabeled compound (I)$^d$ (2.3 mg/kg) and radioactivity was determined by HPLC:
Column: Chromolith Performance RP-18 endcapped 100-4.6 mm monolithic HPLC-column (MERCK)
Solvent: 13% Acetonitrile in H$_2$O (0.1% TFA)
Flow rate: 5 ml/min
UV Detection: 225 nm The time-activity graph is shown in FIG. 2. Activity concentrations in the rat brains (total radio activity) in plasma after the PET Scan were 0.27% ID/g for rat 1 and 0.19% ID/g for rat 2.

What is claimed is:
1. A radiolabeled glutaminylcyclase (QC) inhibitor suitable for use as an imaging agent, wherein:
  a) the radiolabel is selected from the group consisting of $^2$H (D or deuterium), $^3$H (T or tritium), $^{11}$C, $^{14}$C, $^{13}$N, $^{15}$N, $^{15}$O, $^{17}$O, $^{18}$O, $^{35}$S, $^{36}$Cl, $^{82}$Br, $^{75}$Br, $^{76}$Br, $^{77}$Br, $^{123}$I, $^{124}$I, $^{125}$I, and $^{131}$I; or
  b) the radiolabeled inhibitor is a compound of formula (II):

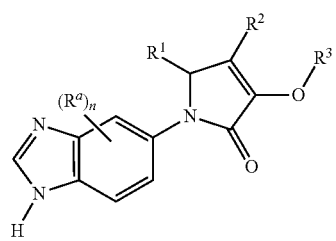

(II)

or a pharmaceutically acceptable salt thereof, including all tautomers and stereoisomers thereof wherein:
  R$^1$ represents —C$_{1-6}$alkyl, -aryl, —C$_{1-6}$alkylaryl, -cycloalkyl, —C$_{1-6}$alkylcycloalkyl, -heteroaryl, —C$_{1-6}$alkylheteroaryl, -heterocyclyl, —C$_{1-6}$alkylheterocyclyl, -cycloalkyl substituted by phenyl, -cycloalkyl substituted by phenoxy, -phenyl substituted by cycloalkyl, -phenyl substituted by phenoxy, -phenyl substituted by phenyl, heterocycyl substituted by phenyl, heteroaryl substituted by phenyl, phenyl substituted by heterocyclyl, phenyl substituted by heteroaryl, phenyl substituted by —O-cycloalkyl, or phenyl substituted by -cycloalkyl-heterocyclyl;
  in which any of aforesaid aryl, cycloalkyl, heterocyclyl, heteroaryl, phenyl, or phenoxy groups may optionally be substituted by one or more groups selected from C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, —SO$_2$C$_{1-4}$alkyl, C$_{1-6}$alkoxy, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{3-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl), and —C(O)NH(C$_{3-10}$cycloalkyl);

R$^2$ represents —C$_{1-6}$alkyl, C$_{1-6}$haloalkyl, -aryl, —C$_{1-6}$alkylaryl, -cycloalkyl, —C$_{1-6}$alkylcycloalkyl, -heteroaryl, —C$_{1-6}$alkylheteroaryl, -heterocyclyl, or —C$_{1-6}$alkylheterocyclyl;

in which any of aforesaid aryl, heteroaryl or heterocyclyl groups may optionally be substituted by one or more groups selected from C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, —SOC$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-8}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$ alkyl-, nitro, halogen, cyano, hydroxyl, —C(O)OH, —NH$_2$, —NHC$_{1-4}$alkyl, —N(C$_{1-6}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl), and —C(O)NH(C$_{3-10}$cycloalkyl);

R$^3$ represents C$_{1-6}$alkyl or C$_{1-6}$haloalkyl;

n represents an integer selected from 0 to 3; and

R$^a$ represents C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, —SO$_2$C$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SO$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl), or —C(O)NH(C$_{3-10}$cycloalkyl); and the radiolabel is selected from the group consisting of $^2$H (D or deuterium), $^3$H (T or tritium), $^{11}$C, $^{14}$C, $^{13}$N, $^{15}$N, $^{15}$O, $^{17}$O, $^{18}$O, $^{35}$S, $^{38}$Cl, $^{82}$Br, $^{75}$Br, $^{76}$Br, $^{77}$Br, $^{123}$I, $^{124}$I, $^{125}$I, and $^{131}$I.

2. The inhibitor of claim 1, which is a compound of formula (II)$^a$:

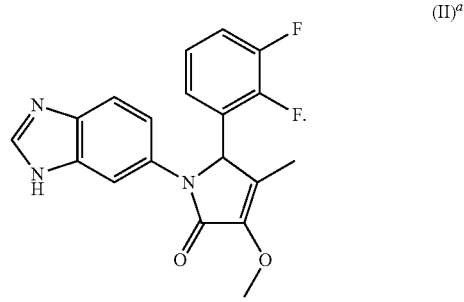 [SMILES: COC1=C(C)C(c2cccc(F)c2F)N(c2ccc3nc[nH]c3c2)C1=O]

(II)$^a$

3. The inhibitor of claim 1, comprising a single radiolabel.
4. The inhibitor of claim 1, wherein the radiolabel is selected from the group consisting of $^{11}$C, $^{120}$I, $^{123}$I, $^{131}$I, $^{75}$Br, and $^{76}$Br.
5. The inhibitor of claim 4, wherein the radiolabel is $^{11}$C.
6. The inhibitor of claim 1, wherein the radiolabel is $^{14}$C.

7. The inhibitor of claim 6, wherein the radiolabeled compound is a compound of formula (II)$^c$:

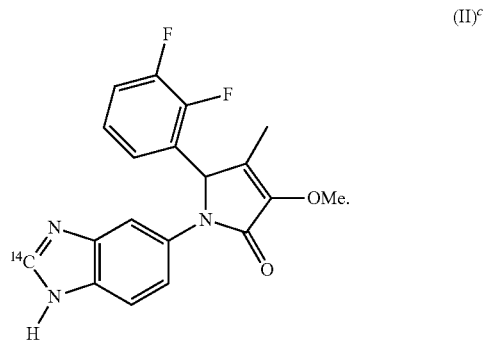 [SMILES: COC1=C(C)C(c2cccc(F)c2F)N(c2ccc3[nH][14cH]nc3c2)C1=O]

(II)$^c$

8. The inhibitor of claim 7, which is a compound of formula (II)$^d$:

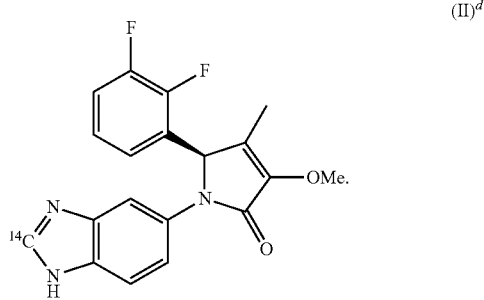 [SMILES: COC1=C(C)[C@H](c2cccc(F)c2F)N(c2ccc3[nH][14cH]nc3c2)C1=O]

(II)$^d$

9. The inhibitor of claim 1, formulated for use as imaging agent in the detection of a neurological disorder.

10. A pharmaceutical composition comprising:
a radiolabeled glutaminylcyclase (QC) inhibitor as defined in claim 1 or a pharmaceutically acceptable salt thereof, including all tautomers and stereoisomers thereof; and
one or more pharmaceutically acceptable excipients.

11. The pharmaceutical composition of claim 10, for use as an imaging agent in the detection of a neurological disorder.

12. The pharmaceutical composition of 11, wherein the neurological disorder is selected from the group consisting of mild cognitive impairment, Alzheimer's disease, Familial British Dementia, Familial Danish Dementia, neurodegeneration in Down Syndrome, and Huntington's disease.

13. The pharmaceutical composition of claim 10, formulated for use in the detection of amyloid peptides.

14. The pharmaceutical composition of claim 10, formulated for use in the detection of tau proteins of neurofibrillary tangles.

15. A method for detection of (i) senile plaques or neurofibrillary tangles in a brain tissue, (ii) amyloid deposits in a brain tissue, or (iii) tau proteins in a brain tissue, the method comprising:
contacting brain tissue and a radiolabeled glutaminylcyclase (QC) inhibitor as defined in claim 1;
wherein at least one of the following is satisfied
detection is in vivo; following administration of a radiolabeled glutaminylcyclase (QC) inhibitor to a patient detection is ex vivo;
detection is in vitro;
the inhibitor is formulated for detection of the neurofibrillary tangles;
the inhibitor is formulated for detection of neurological disorders;
the inhibitor is formulated for detection of tau aggregates;
the inhibitor is formulated for detection of amyloid deposit;
detection comprises measuring the affinity of the inhibitor for senile plaques;
detection comprises measuring the affinity of the inhibitor for tau aggregates;
detection comprises detecting the binding level of the inhibitor to the amyloid deposit;
detection comprises detecting the binding level of the inhibitor to tau proteins;
detection comprises using gamma imaging, magnetic resonance imaging, magnetic resonance spectroscopy or fluorescence spectroscopy; or
detection comprises using gamma imaging selected from PET and SPECT.

16. A kit for diagnosing a neurological disorder which comprises a pharmaceutical composition as defined in claim 10 and instructions for detection of senile plaques or neurofibrillary tangles in a brain tissue, amyloid deposits in a brain tissue, or tau proteins in a brain tissue.

17. The kit of claim 16, wherein the neurological disorder is selected from the group consisting of mild cognitive impairment, Alzheimer's disease, Familial British Dementia, Familial Danish Dementia, neurodegeneration in Down Syndrome, and Huntington's disease.

* * * * *